United States Patent
Liu

(10) Patent No.: US 10,780,444 B2
(45) Date of Patent: Sep. 22, 2020

(54) SYSTEM AND METHOD FOR DETECTION OF CELLS

(71) Applicant: Microsensor Labs, LLC, Chicago, IL (US)

(72) Inventor: Peng Liu, Chicago, IL (US)

(73) Assignee: Microsensor Labs, LLC, Chicago, IL (US)

( * ) Notice: Subject to any disclaimer, the term of this patent is extended or adjusted under 35 U.S.C. 154(b) by 73 days.

(21) Appl. No.: 15/862,394

(22) Filed: Jan. 4, 2018

(65) Prior Publication Data

US 2018/0185854 A1   Jul. 5, 2018

Related U.S. Application Data

(60) Provisional application No. 62/442,818, filed on Jan. 5, 2017.

(51) Int. Cl.
*B03C 1/005* (2006.01)
*B01L 3/00* (2006.01)
(Continued)

(52) U.S. Cl.
CPC ........... *B03C 1/005* (2013.01); *A61M 1/3403* (2014.02); *B01L 3/502761* (2013.01);
(Continued)

(58) Field of Classification Search
CPC ....... B03C 1/005; B03C 1/02; B03C 2201/24; B03C 1/01; B03C 2201/26;
(Continued)

(56) References Cited

U.S. PATENT DOCUMENTS

| 2004/0262210 A1 | 12/2004 | Westervelt et al. |
| 2006/0020371 A1 | 1/2006 | Ham et al. |

(Continued)

FOREIGN PATENT DOCUMENTS

| EP | 2073016 | * | 6/2009 | ............. G01N 35/00 |
| EP | 2073016 A1 | | 6/2009 | |

(Continued)

OTHER PUBLICATIONS

Hakho Lee, IC/Microfluidic Hybrid System for Magnetic Manipulation of Biological Cells, Jun. 2006, IEEE Journal of Solid-State Circuits, vol. 41, No. 6, pp. 1-9 (Year: 2006).*

(Continued)

*Primary Examiner* — Claire A Norris
*Assistant Examiner* — Ekandra S. Miller-Cruz
(74) *Attorney, Agent, or Firm* — Lempia Summerfield Katz LLC

(57) ABSTRACT

A system and method for detection of cells is disclosed. Target cells, such as circulating tumor cells (CTCs), may be of interest. Magnetic beads may be bound to the target cells. After which, the target cells (with the magnetic beads attached thereto) may be identified using an applied magnetic field. In one example, magnetic sensors may be used to detect movement of the target cells responsive to an applied magnetic field. In another example, an optical sensor (such as a camera) may be used to detect movement of the target cells responsive to an applied magnetic field. Further, separate from identification of the target cells, the target cells may be sorted using an applied magnetic field. In this way, a magnetic field may be used in either or both of target cell identification or target cell sorting in order to detect target cells of interest.

18 Claims, 27 Drawing Sheets

(51) Int. Cl.
*G01N 15/14* (2006.01)
*G01N 15/10* (2006.01)
*G01N 27/74* (2006.01)
*A61M 1/34* (2006.01)
*C12M 1/26* (2006.01)
*G01N 33/49* (2006.01)
*G01N 33/574* (2006.01)
*G01N 33/543* (2006.01)

(52) U.S. Cl.
CPC ......... *C12M 1/266* (2013.01); *G01N 15/1056* (2013.01); *G01N 15/1463* (2013.01); *G01N 27/745* (2013.01); *G01N 33/491* (2013.01); *G01N 33/57415* (2013.01); *G01N 33/57492* (2013.01); *B01L 2200/0668* (2013.01); *B01L 2300/0663* (2013.01); *B01L 2300/089* (2013.01); *B01L 2300/0816* (2013.01); *B01L 2400/043* (2013.01); *G01N 33/54326* (2013.01); *G01N 2015/1006* (2013.01); *G01N 2015/1081* (2013.01)

(58) Field of Classification Search
CPC ........... B03C 2201/18; B01L 3/502761; B01L 2300/0663; B01L 2400/043; B01L 2200/0668; B01L 2300/089; B01L 2300/0816; B01L 3/5027; B01L 3/5023; B01L 3/502707; B01L 3/502753; B01L 3/502784; B01L 2200/026; B01L 2200/027; B01L 2200/04; B01L 2200/0647; B01L 2200/10; B01L 2300/02; B01L 2300/023; B01L 2300/024; B01L 2300/025; B01L 2300/06; B01L 2300/0627; B01L 2300/0654; B01L 2300/0861; B01L 3/502715; B01L 2300/1833; A61M 1/3403; C12M 1/266; G01N 2015/1081; G01N 2015/1006; G01N 15/1056; G01N 15/1463; G01N 27/745; G01N 33/57415; G01N 33/57492; G01N 33/491; G01N 33/54326
USPC .................. 210/94, 695, 167.03, 222, 748.05
See application file for complete search history.

(56) References Cited

U.S. PATENT DOCUMENTS

| | | |
|---|---|---|
| 2008/0246470 A1 | 10/2008 | Kahlman et al. |
| 2010/0006439 A1* | 1/2010 | Ham ............... B01L 3/502761 204/547 |
| 2010/0255556 A1 | 10/2010 | Hunt et al. |
| 2011/0018532 A1 | 1/2011 | Florescu et al. |
| 2014/0248632 A1 | 9/2014 | Kopelman et al. |
| 2015/0219544 A1* | 8/2015 | Liu ............... G01N 15/1031 506/39 |
| 2015/0253284 A1* | 9/2015 | Sudarsan ......... B01L 3/502792 204/450 |

FOREIGN PATENT DOCUMENTS

| | | |
|---|---|---|
| EP | 2488866 B1 | 4/2015 |
| WO | 03039753 A1 | 5/2003 |

OTHER PUBLICATIONS

Liu, P. (2012). "Magnetic Relaxation Detector for Microbead Labels." IEEE J Solid-State Circuits. 47(4): 1056-1064.
U.S. Office Action for U.S. Appl. No. 14/171,661, dated Apr. 30, 2015.
U.S. Office Action for U.S. Appl. No. 14/171,661, dated Aug. 27, 2015.
PCT International Search Report for PCT Application No. PCT/US2018/012340.
PCT Written Opinioni for PCT Application No. PCT/US2018/012340.
Lee, Hakho, et al. "An IC/microfluidic hybrid microsystem for 2D magnetic manipulation of individual biological cells." Solid-State Circuits Conference, 2005. Digest of Technical Papers. ISSCC. 2005 IEEE International. IEEE, 2005.
Lee, Hakho, et al. "IC/microfluidic hybrid system for magnetic manipulation of biological cells." IEEE Journal of Solid-State Circuits 41.6 (2006): 1471-1480.
Lee, Hakho, et al. "Integrated cell manipulation system—CMOS/microfluidic hybrid." Lab on a Chip 7.3 (2007): 331-337.
Liu, Yong, et al. "IC/microfluidic hybrid system for biology." Bipolar/BiCMOS Circuits and Technology Meeting, 2005. Proceedings of the. IEEE, 2005.
Reyes, Darwin R., et al. "Micro total analysis systems. 1. Introduction, theory, and technology." Analytical chemistry 74.12 (2002): 2623-2636.

* cited by examiner

Cell Detection (Magnetic)
220

Cell Enrichment (Magnetic)
210

200

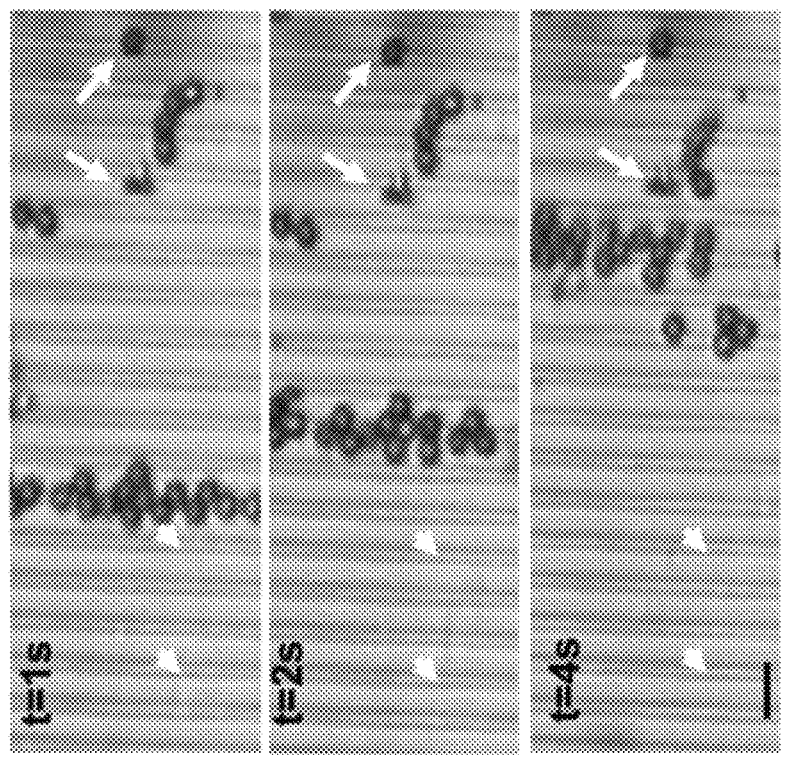

SYSTEM AND METHOD FOR DETECTION OF CELLS

REFERENCE TO RELATED APPLICATION

This application claims the benefit of U.S. Provisional Application No. 62/442,818 filed on Jan. 5, 2017, the entirety of which is incorporated by reference herein.

BACKGROUND

Every year, more than $250 billion is spent on cancer treatment in the United States. In general, more than 90% of cancer-related deaths are related to metastasis. Research on circulating tumor cells (CTCs), the metastatic precursors in the bloodstream, can potentially be pivotal in managing this disease as it aids in early cancer detection, personalized medicine and minimal residual disease monitoring. Compared to fresh tissue biopsy, "liquid biopsy" of CTCs in blood samples is much more accessible and affordable, and is much less invasive. During the past ten years, CTCs have received attention as new biomarkers and the subject of basic research. Some studies indicate that the systematic dissemination of cancer can occur early during cancer progression. Other clinical studies show that CTC counts can be used as a prognostic indicator of survival for a variety of cancers. Despite the significant clinical relevance of CTCs, their clinical utility is hampered by low sensitivity, requisite sample purification and high instrument cost.

BRIEF DESCRIPTION OF THE DRAWINGS

The accompanying drawings, which are incorporated in and constitute a part of this specification, illustrate various aspects of the invention and together with the description, serve to explain its principles. Wherever convenient, the same reference numbers will be used throughout the drawings to refer to the same or like elements.

FIG. 5B illustrates one example of on-chip bead manipulation.

DETAILED DESCRIPTION OF EMBODIMENTS

Overview

Figure 1A:
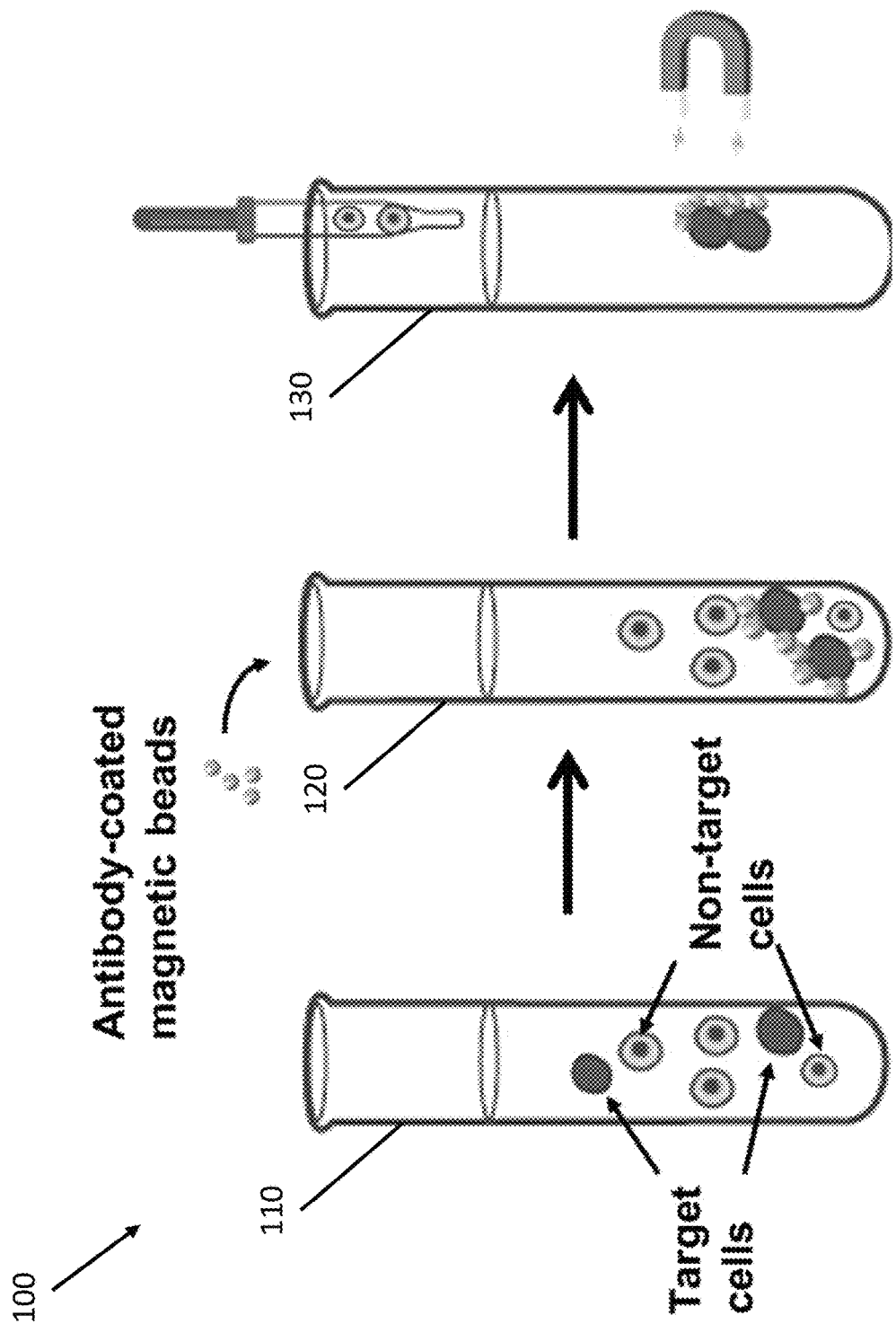
FIG. 1A is an illustration of binding magnetic beads to target cells and to cell isolation (e.g., enrichment) of the target cells.

Analysis and/or sorting of cells (such as rare cells) may be applied to any one, any combination, or all of the following areas: oncology; immunology; neurobiology; stem cell biology; and developmental biology. For instance, functional studies and molecular analysis of circulating tumor cells (CTCs) at the single-cell level may potentially lead to early cancer detection and guide the targeted therapy. In stem cell biology, it may be beneficial to assess a cell's self-renewal and differentiation potential at single-cell resolution. Research on rare cells such as circulating fetal cells, antigen-specific T- or B-cells, and disseminated tumor cells (DTCs), cells infected by virus or parasites are potentially of importance to the advancement in diagnosis, prognosis and therapeutics.

The below discussion focuses on identifying CTCs in a sample. However, the systems and methods disclosed herein may be used for identification of other items of interest. For example, the discussed systems and methods may be used to identify a variety of cells, such as bacteria cells. Other examples of cells of interest include fetal cells, stem cells, antigen-specific T- or B-cells, and the like. Thus, in one implementation, the system and method may be used to identify any target cell that may be tagged with a marker or other type of particle (e.g., any type of magnetic marker or other type of magnetic particle), such as an antibody coated magnetic bead. In this regard, any discussion below regarding isolation, identification, and/or sorting with regard to CTCs may be equally applied to any target cell of interest. Further, the cells may be resident in a variety of fluids. As one example, the cells may be resident in a blood sample. As another example, the cells may be resident in a water sample. Thus, any discussion below regarding processing a blood sample may be equally applied to any other type of sample (e.g., a fluid sample), such as a water sample.

With regard to CTCs, due to the scarcity of CTCs (e.g., as few as one CTC per billion blood cells in the circulation of patients with advanced cancer), detection and enumeration of CTCs may be preceded by a cell isolation (e.g., enrichment) step. Immunomagnetic cell isolation is one technique to enrich rare cells of interest from a heterogeneous cell population and is adopted by many CTC detection systems. In this technique, cell suspension is first mixed with magnetic beads conjugated with antibodies that bind specifically to target cell surface antigens, followed by exposure of the suspension to a magnet to isolate the target cells. However, due to the lack of analytical capabilities in the magnetic isolation, during the detection step, most CTC detection systems rely on optical methods (e.g., fluorescent imaging), which requires extensive sample processing (e.g. cell fixation and immunostaining) and often leads to the loss of target cells, the decay of biomarkers and the degradation of assay sensitivity and specificity. In addition, in such a system, the CTCs may not suitable for downstream molecular analysis. In particular, applying fluorescent biomarkers for optical analysis may kill the cells subject to analysis. This may result in downstream molecular analysis becoming more difficult to perform (e.g., in DNA downstream processing) or becoming impossible to perform (e.g., RNA downstream processing).

In this regard, in one implementation, cell isolation is performed while maintaining the viability of the cells subject to analysis. Specifically, in one implementation, a system and method is disclosed which directly detects the bead-labeled target cells. In particular, the system and method may include one or more structures and/or one or more processes that enable the detection of the bead-labeled target cells.

In a first specific implementation, the system includes one or more wells and one or more sensors that work in combination to enable detection of the bead-labeled target cells. As discussed in more detail below, the sensor may comprise a Hall effect sensor (or a series of Hall effect sensors), a Giant Magnetoresistance (GMR) sensor, or a Superconducting Quantum Interference Device (SQUID) sensor. The sensors may be configured to sense at least one magnetic characteristic. Further, the sensors listed are merely for illustration purposes. Other types of magnetic sensors are contemplated. The surface area of the sensor (or group of sensors that act in combination) may be much larger than the size of the target cell subject to detection. In on implementation, a sensor unit (e.g., a "pixel") is approximately the same size as or even smaller than single bead. Further, the total area of the sensor array may be much larger than a single target cell.

In a specific implementation, the chip may have a total area that can detect more than hundreds (e.g., 500) target cells simultaneously. For example, the chip may include the sample well designed to hold as many as 500 bead-bound Caco-2 cells. The particles may be placed onto the surface of the chip sensing area in the well, such as by gravity, and their magnetic signals may be detected by the underlying sensor units. Bead-bound target cells may be differentiated from contaminants by signal strength and number of pixels and then moved in certain path (see discussion below regarding FIG. 6).

With regard to the chip design, the following are considerations. First, each of the long metal lines on the chip may be modelled as a metal resistor, so they are subject to voltage drop and will also generate heat when current flowing through. For instance, a 5 mm-long 2 μm-wide metal line in 0.18 μm CMOS process can have a resistance more than 120Ω. If 30 mA is injected into the wire, then there will be 3.6V voltage drop. This might cause issues if the chip is powered with a 3.3V supply. On the other hand, the heat generated by the metal wires will increase the sample temperature and might affect cell viability. Therefore, the metal lines are designed to balance these design parameters.

Second, the detection errors of the sensor array may be negligible compared to assay result variation. The detection errors of a sensor array may be strongly dependent on the total number of unit sensors and signal-to-noise ratio (SNR) of individual sensors. For instance, the probability of detection error may be less than 0.1% with a sensor SNR of 15.9 dB. The sensor outputs on the chip may be read out in parallel to achieve high throughput.

As discussed above, the system and method may identify various target cells. In one example, the target cells subject to identification may range in size from 20 microns to 50 microns. Other sizes are contemplated. In this example, the surface area of the sensor (or group of sensors) may be at least an order of magnitude greater than the size of the target cells (such as in one implementation, at least two orders of magnitude greater; such as in another implementation, at least three orders of magnitude greater; such as in still another implementation, at least four orders of magnitude greater, etc.).

The structure of the well(s) may be designed to work in combination with a sensor (or group of sensors), which has a surface area that is much greater than the size of the target cell. Typically, a focusing device, such as focusing device 44 disclosed in US Published Application No. 2015/0219544 (incorporated by reference herein in its entirety), is used to focus each target cell one-by-one on a central area of the sensor for detection of the target cells. Because the surface area of the sensor (or group of sensors) is much greater than the size of the target cell, a focusing device that uses a series of wires to magnetically manipulate the target cells to the middle of the sensor is unnecessary. In this regard, the system need not include wiring or other structure to magnetically manipulate the target cells through an inlet to the geometric center of the sensor (thereby channeling the target cells one-by-one to the geometric center of the sensor). Rather, the well(s) may include an inlet and/or outlet that generally guides the target cells onto the surface area of the sensor(s), without channeling the target cells individually or to a specific section of the sensor(s). Thus, a variety of means may be employed by which to guide the target cells onto the surface of the sensor(s), such as by gravity, by forced air, by magnetic manipulation (without the need to channel the target cells one-by-one or to the center of the sensor(s)). As one example, a blood sample, a water sample, or the like may be dropped into the well so that gravity may be used to guide the sample into the well.

As discussed above, the system and method may use the magnetic beads (bonded to the target cells) as part of the detection process. In one implementation, the system may use magnetic sensor(s) (such as a group of Hall effect sensors) without magnetic manipulation to detect the bead-labeled target cells. For example, the Hall effect sensor(s), whose area is much larger than the size of the target cell, may detect multiple bead-labeled target cells simultaneously, such as all of the bead-labeled target cells in the well simultaneously (as opposed to one-by-one), resulting in faster detection of the bead-labeled target cells.

In an alternate implementation, the system may use magnetic manipulation in order to detect the bead-labeled target cells. More specifically, the system may detect the bead-labeled target cells by applying a magnetic field and then analyzing whether there is movement of cells. Detection of movement may be based on one or both of the following: (1) magnetic analysis (e.g., Hall effect sensor output); or (2)

visual analysis (e.g., analyzing pictures before and after the magnetic field is applied). For example, one or more sets of wires may generate a magnetic field on a part of the well. A sensor (such as a magnetic sensor, an optical sensor (e.g., a camera), or the like) may take one or more readings in order to detect the bead-labeled target cells.

In the example of a magnetic sensor (such as a Hall effect sensor), the system may read the output of the magnetic sensor without an applied magnetic field, read the output of the magnetic sensor with an applied magnetic field, and compare the two readings. Alternatively, the system may read the output of the magnetic sensor with a first applied magnetic field, read the output of the magnetic sensor with a second applied magnetic field, and compare the two readings. For example, the system may control the current (thereby modifying the applied magnetic field in order to manipulate which items (e.g., free beads or bead-labeled target cells) are detected). In particular, the system may use varying currents (e.g., first a lower current to detect the movement of the free beads and then a higher current to detect the bead labeled target cells). Thus, the system may vary the AC current magnitude and/or vary the AC current frequency in detecting the bead-labeled target cells.

In the example of an optical sensor, the system may obtain a first image from the optical sensor without an applied magnetic field, a second image from the optical sensor with an applied magnetic field, and compare the first and second images. Alternatively, the system may obtain a first image from the optical sensor with a first applied magnetic field, a second image from the optical sensor with a second applied magnetic field, and compare the first and second images. Thus, using the optical sensor, the magnetic quality of the bead-labeled target cells may be used in a visual detection. Further, capitalizing on the magnetic quality of the bead-labeled target cells allows for a more simple visual detection, avoiding additional fluorescence tagging when performing visual detection.

In a system that applies a magnetic field, the electronics to generate a magnetic field may be positioned in one of several ways. In one way, the electronics may be positioned on a level that is different from the magnetic sensor electronics. For example, the Hall effect sensor may be positioned on one level, such as on the substrate/active layer of the electronics, and the electronics to generate the magnetic field may be positioned on a different level (e.g., the wiring to generate the magnetic field may be on another level of the CMOS electronics.

Further, the system may include the magnetic sensor, the wells, and the readout electronics. For example, the sample well may be created by sandwiching a microchip between an insulating support (such as a plastic layer) and an insulating cover (with the cover including a hole for the opening of the well). The microchip may be electronically connected to a flex board, which may provide the readout electronics (e.g., a micro USB connector or other output). As discussed in more detail below, this type of sandwiching creates a well with various dimensions, such as a 1 cm×1 cm area well, with a height of ½ cm.

In one implementation, the system may reduce the number of free beads in the fluid. As discussed above, beads, such as magnetic beads, may be applied to the fluid (such as to a blood sample). Some of the beads may bind to the target cells (e.g., the CTCs), thereby becoming bound to the target cells. Other beads (such as the large majority of the beads applied to the fluid) may not bind to any other cell, and become free beads (e.g., unbound beads that are in the fluid). In one optional implementation, after applying the unbound beads to the fluid, the system may perform one or more steps in order to reduce the number of free beads in the fluid. As discussed in more detail below, one or more procedures, such as filtering the fluid (e.g., collecting the free beads in a filter), applying a centrifugal force (e.g., by using a centrifuge to separate the free beads from other particles in the fluid), and/or applying a magnetic force to separate the free beads from other particles in the fluid. In one implementation, reduction in the number of free beads may be performed after the cell isolation step and before the cell identification step. In an alternate implementation, reduction in the number of free beads may be performed after the cell isolation step and the cell identification step, but before the cell sorting step.

In yet another implementation, after performing the cell isolation step, the system may perform a cell sorting step. Cell sorting, such as single cell sorting, may be focused on any one, any combination, or all of: yield; purity; cell viability; and throughput. However, conventional technologies may require abundant target cell populations or high-purity starting samples and thus have limited capabilities to isolate and analyze rare cells. For instance, a single CTC can be surrounded by millions of leukocytes and billions of erythrocytes in peripheral blood. However, fluorescent-activated cell sorting (FACS) usually requires more than 10,000 target cells in the starting sample due to significant cell loss; micromanipulation, limiting dilution and laser microdissection are effective only on high-purity cell populations, and are time consuming and low-throughput.

With regard to cell viability, ideally, the isolated cells should be viable for downstream molecular analysis of genomics, transcriptomics and proteomics. Cell viability is also essential in cell-base assays and cell line development. One of the most well-known examples is the production of monoclonal antibody where target cell populations grow from a single live cell. However, typically, single cell sorting technologies use fixation and/or staining (e.g., in fluorescent activated cell sorting or FACS) which usually leads to loss of cell viability.

Therefore, an easy-to-use and/or high-throughput tool to isolate and sort single intact and viable rare cells, discussed below, has wide applications in bioscience research and clinical benefit. Specifically, the tool may include a cell sorting step that uses magnetic manipulation in order to sort one or more cells of interest (e.g., the CTCs bound to the beads). As discussed in more detail below, the magnetic manipulation may guide the cells of interest within the well to one or more chambers for sorting.

In still another implementation, the system may detect multiple types of bead-labeled target cells. As discussed above, a bead may be bound to a target cell. In a more specific implementation, a first bead may be bound to a first target cell, and a second bead may be bound to a second target cell. The system may detect the first bead bound to the first target cell along with (e.g., simultaneously) detecting the second bead bound to the second target cell. In this regard, the first and second beads may be used for cell isolation (e.g., enrichment) and for detection of multiple targets (e.g., with the different bead labels). As discussed in more detail below, one method of detection comprises varying frequency in order to detect the different bead labeled target cells, such as based on different response times for the different bead labeled target cells.

Embodiments

As discussed above, due to the scarcity of CTCs (as few as one CTC per billion blood cells in the circulation of patients with advanced cancer), detection and enumeration of CTCs may be preceded by a cell isolation (e.g., enrichment) step. Immunomagnetic cell isolation is one technique to enrich rare cells of interest from a heterogeneous cell population. For example, the cell isolation (e.g., enrichment) step may increase the purity of sample based on immuno-affinity. In this technique, cell suspension is first mixed with magnetic beads conjugated with antibodies that bind specifically to target cell surface antigens, followed by exposure of the suspension to a magnet to isolate the target cells. This is illustrated by 100 in FIG. 1A, which at 110 shows the target and non-target cells. As discussed above, the numbers of non-target cells may be many orders of magnitude greater than the numbers of target cells. 120 illustrates magnetic beads conjugated with antibodies that bind specifically to target cell surface antigens, are mixed with the cell suspension. 130 illustrates the followed step of exposure of the suspension to a magnet to isolate the target cells.

Figure 1B:
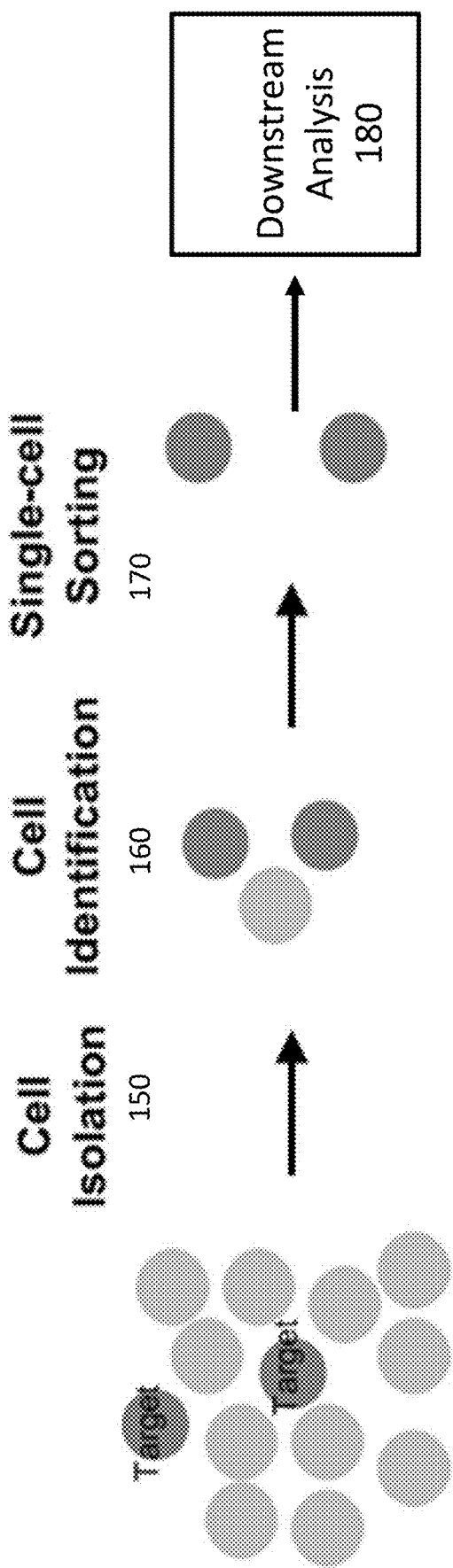
FIG. 1B illustrates various steps in the processing including cell isolation, cell identification, cell sorting (such as single cell sorting), and downstream analysis.

Thus, the fluid (such as the blood sample) may be subject to one or more steps. FIG. 1B illustrates various example steps including cell isolation, cell identification, cell sorting (such as single cell sorting), and downstream analysis. In particular, target cells may first be enriched with automated magnetic cell isolation technique. The sample after elusion may then be transferred to a sample well where an embedded magnetic sensor chip, discussed below, may detect the bead-bound target cells by their magnetic signal. Further, the magnetic sensor chip may then sort individual target cells with spatially-patterned microscopic magnetic field generated by on-chip metal wires. Optionally, a free bead reduction step may be included, such as after cell isolation and before cell identification. The cell isolation step (e.g., the cell enrichment step) may comprise the step of binding the beads (e.g., the magnetic beads) to the target cells. In a specific implementation, the cell isolation step comprises the tagging of the beads to the CTCs. In a blood sample, the large majority of cells are not CTCs, instead being other cells, such as white blood cells. Likewise, the blood sample may include contaminants. The cell isolation step may result in binding of the magnetic beads to some of the CTCs within the blood sample, such as approximately 90% of CTCs. The cell identification step may comprise identifying the target cells that have been tagged or had beads bound to them. The cell sorting step may comprise sorting the target cells that have been tagged or had beads bound to them, such as single cell sorting that sorts one tagged CTC at a time.

Further, the magnetic cell processing/isolation may be used in a high-throughput cell isolation technique. Because no cell fixation or labeling is necessary for the following steps, the sample processing time in cell identification is reduced. Further, the magnetic tag allows the target cells to move rapidly with precisely controlled microscopic magnetic field on chip. The assay time to isolate, identify and sort 100 single spiked cancer cells from blood sample may be approximately 3 hours (versus 12-25 hours for other techniques). Moreover, all three steps (cell isolation, cell identification, single-cell sorting) may be scalable and automated. For instance, a magnetic cell isolation protocol may be implemented with an automated magnetic particle processor. In one implementation, up to 12 samples may be processed on these automated magnetic particle processor systems simultaneously.

In one implementation, all the steps, including the cell isolation step, the cell identification step, and the cell sorting step are performed in a discrete and separate manner. In such an implementation, after the cell isolation step, each of the cell identification step and cell sorting step at least party use the magnetic property of the beads bound to the target cells for processing. In particular, the cell isolation step may use the magnetic property of the beads (either in combination with an optical sensor or in combination with a magnetic sensor) and the cell sorting step may use the magnetic property of the beads. Alternatively, only one of the cell identification step and cell sorting step at least party uses the magnetic property of the beads bound to the target cells for processing. For example, only the cell identification step uses the magnetic property of the beads bound to the target cells for processing, whereas the cell sorting step does not use the magnetic property of the beads bound to the target cells for processing (e.g., the cell sorting step uses a gripper to manually grip the identified bound CTCs). As another example, the cell identification step does not use the magnetic property of the beads bound to the target cells for processing, whereas the cell sorting step uses the magnetic property of the beads bound to the target cells for processing.

In an alternate implementation, some of the steps, such as the cell identification step and the cell sorting step are performed in combination. For example, the cell identification step and the cell sorting step may be performed in the same step.

Referring back to FIG. 1B, the steps may comprise: cell isolation 150; cell identification 160; single cell sorting 170; and downstream analysis 180. Examples of downstream analysis include, but are not limited to cell culture, protein analysis (e.g., proteomics), and DNA/RNA analysis (e.g., genomics and transcriptomics). Other types of downstream analysis are contemplated.

In one implementation, magnetic cell isolation may comprise cell enrichment technique for BULK isolation of pure, viable and functional cells. In magnetic cell isolation, magnetic particles (microbeads or nanoparticles) conjugated with biomarkers that bind specifically to target cell surface may be mixed with the cell suspension, followed by exposure of the suspension to a magnet to isolate the target cells, such as illustrated in FIG. 1A. For instance, anti-epithelial cell adhesion molecule (EpCAM) may be used in many CTC isolation platforms since EpCAM expression is virtually universal in cells with epithelial origin but absent in blood cells. Unlike other high-throughput techniques such as Fluorescence-activated cell sorting (or FACS), magnetic cell isolation does not require highly engineered fluidic, optic and electronic system for operation.

Figure 2A:
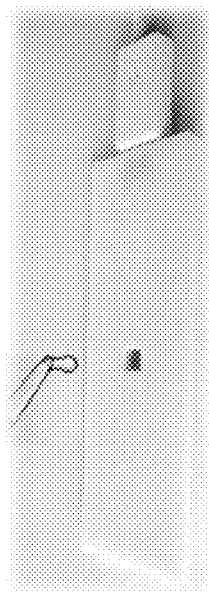
FIG. 2A is one illustration of the stages of cell isolation (e.g., enrichment) and detection using the magnetic beads.
Figure 2A:
Figure 2A:

After the cell isolation (e.g., enrichment) step, the system may detect and/or enumerate the CTCs using the magnetic beads. In particular, the system comprises a microelectronic-chip based magnetic cytometer that may directly detect the immunomagnetically labeled target cells. Due to minimal sample processing and inherently negligible magnetic background of biological samples, the disclosed cytometer enables rapid isolation and detection of rare cells with high sensitivity and specificity while keeping the cells viable to facilitate downstream analysis and cell culture. In addition, since the magnetic sensing technique does not require an optical instrument and special imaging methods, both system and assay cost may be lower than systems that rely on optical instruments. Thus, a system 200, such as illustrated in FIG. 2A, may be used whereby after enrichment (210), cell detection (220) may be performed using the magnetic beads.

Figure 2B:
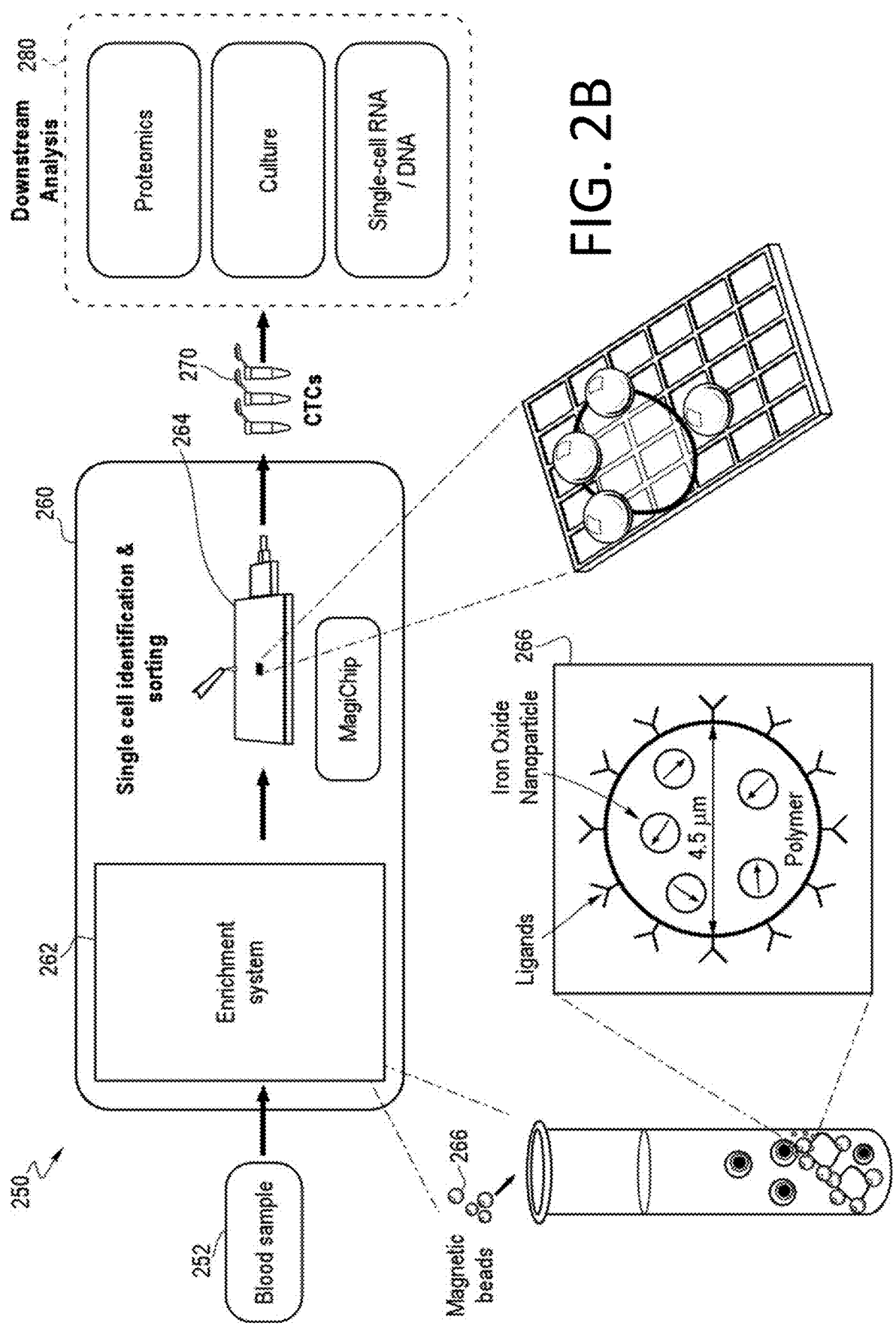
FIG. 2B is another illustration of the stages of cell isolation (e.g., enrichment) and detection using the magnetic beads.

FIG. 2B is another illustration of a system 250 that performs the stages of enrichment and detection using the magnetic beads. Specifically, whole blood 252 may be input to device 260 that includes enrichment system 262 and single cell identification and sorting 264. With regard to enrichment system 262, beads 266 are added to the whole blood 252. An exploded view of the beads 266 is illustrated in FIG. 2B. Specifically, the bead 266 is approximately 4.5 μm, with ligands that may be configured to bind to CTCs. Further, bead 266 may include a magnetic nanoparticle (such as an iron oxide nanoparticle) in order to provide the bead 266 its magnetic property.

In one implementation, enrichment system 262 automates the magnetic cell isolation process, including but not limited to any one, any combination, or all of: washing beads in buffer; conjugating antibodies to beads; mixing beads with sample; washing sample with buffer; and re-suspending sample. For optimized assay performance, the temperature of the magnetic particle processor may be set at low temperature (e.g., 4° C.) or the magnetic particle processor may be placed in a cold room (e.g., 4° C.).

In one implementation, bead preparation (at for example 4° C.) may comprise: (1) taking out 10 μL of stock beads, use 500 μL of buffer 1 to wash beads; (2) adding 1 μL antibody to the beads, then add 30082 L buffer 1; (3) rotating mixing for 1 hour; (4) using magnet to enrich sample and wash with buffer 1; (5) re-suspend sample in 20 μL buffer 1.

In one implementation, isolation of target cell from blood (at for example 4° C.) may comprise: (6) adding 10 μL beads from step (5) to 300 μL blood sample, mixing for 30 minutes; (7) using magnet to enrich sample and wash; and (8) re-suspend sample into 50 μL buffer 2.

After enrichment system 262, single cell identification and sorting 264 may apply a magnetic field (H), such as via one or more wires, and may detect the movement of the magnetic particles, such as via one or more sensors. The output of single cell identification and sorting 264 may comprise the CTCs 270 that have beads 266 bound thereto. The CTCs 270 may be input to downstream analysis 280, which may comprises proteomics, culture, and/or single cell RNA/DNA, as discussed above.

Figure 3A:
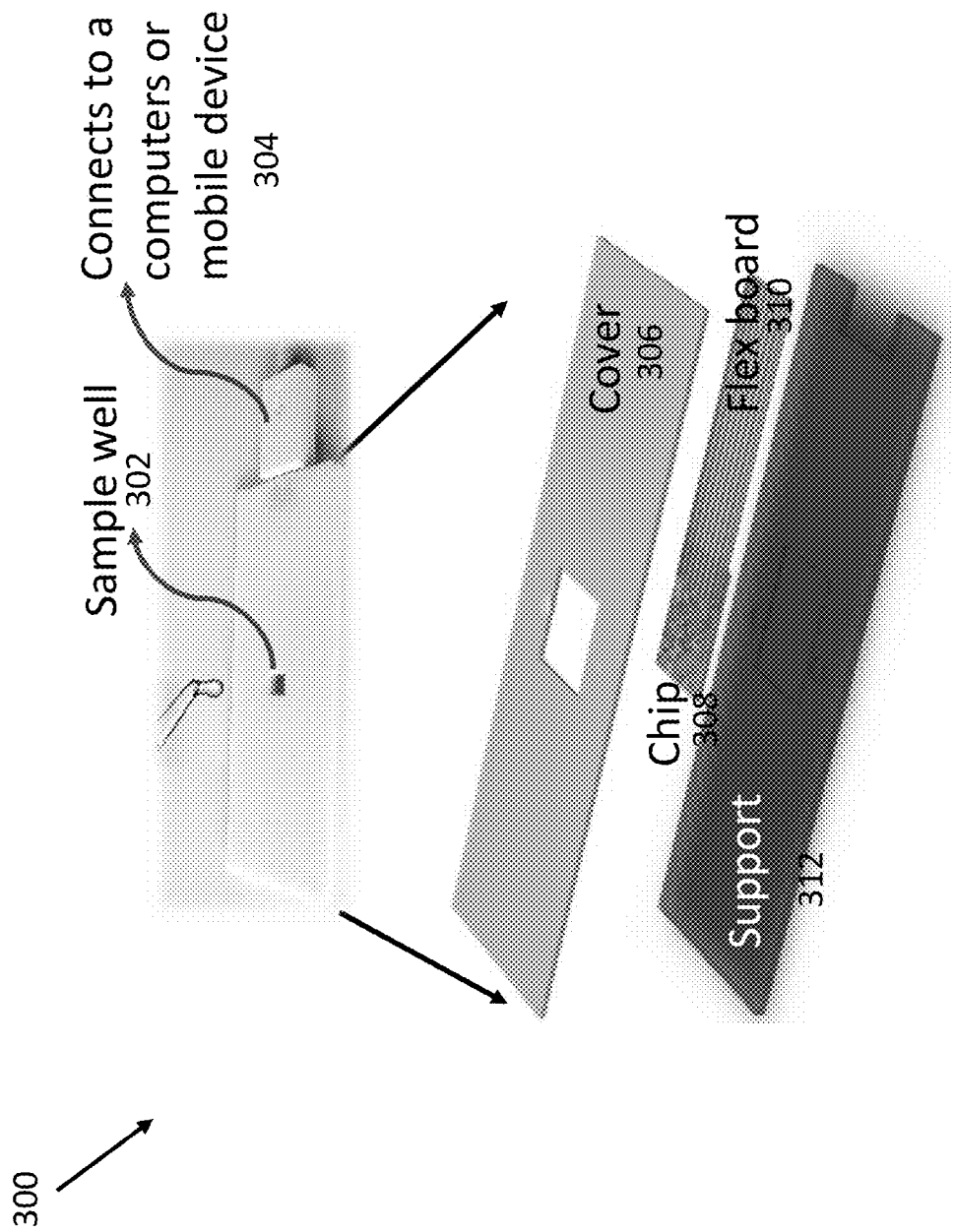
FIG. 3A is an exploded view of an example sensing system in which a microelectronic chip is packaged onto a flex circuit board through flip-chip technology.

FIG. 3A is an exploded view of an example sensing system 300 in which a microelectronic chip 308 is packaged onto a flex circuit board 310 through flip-chip technology. The other side of the flex board may be connected to computer or mobile device 304 through microUSB or other type of interface. An example of computer or mobile device 304 comprises analytics/sorting system 360, illustrated in FIGS. 3B-C. As shown, the chip and flex circuit board 310 are sandwiched by a cover 306 and a support plastic 312. The chip sensing area is exposed through the opening in the cover panel 306 and forms a sample well 302, such as illustrated in FIG. 2A. In one implementation, sensing system 300 may be the same size as that of a microscope slide so that sensing system 300 fits into a typical microscope stage in order to obtain the optical image Thus, the sensing system 300 may include a magnetic bead detector chip for magnetic immunoassays. The chip may be fabricated in a CMOS (complementary metal-oxide-semiconductor) process. As discussed in further detail below, the magnetic bead detector chip may be used in combination with one or more magnetic detection methods in order to detect single magnetic beads on the chip surface. As shown in FIG. 3A, there are three components, including a magnet, a magnetic sensor and a control/readout electronic circuit, to detect a superparamagnetic bead.

In this regard, magnetic detection may be highly sensitive even with minimum sample processing because most biological samples or contaminants (e.g., dusts and debris) have negligible magnetic properties and thus background noise may be very low. The Hall-effect sensor chip illustrated in FIG. 3A may be fabricated in standard semiconductor process that can detect single microbead label in magnetic immunoassays with sensitivity comparable to that of micro-Hall detector (even though the surface area of the Hall-effect sensor chip illustrated in FIG. 3A is more than an order of magnitude (such as more than two orders of magnitude greater).

Figure 3B:
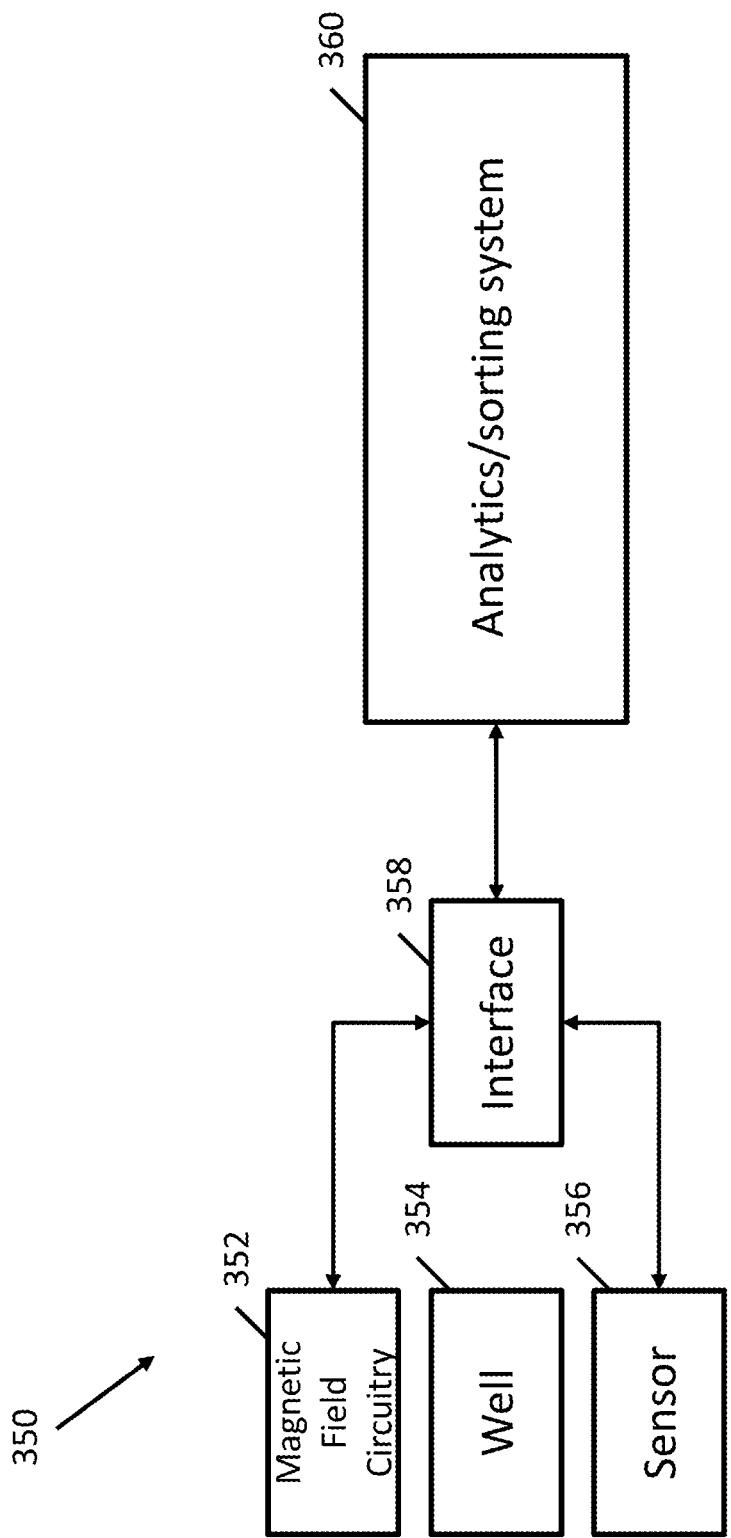
FIG. 3B illustrates a block diagram of the system, including magnetic field circuitry, a well, a magnetic sensor, an electronic interface and an analytics system.

FIG. 3B illustrates a block diagram of the system 350, including magnetic field circuitry 352 (such as wires), a well 354, sensor 356 (e.g., a magnetic sensor (such as a Hall effect sensor); an optical sensor; etc.), an electronic interface 358 (such as a USB interface) and an analytics/sorting system 360. The analytics system may include a processor and a memory (further illustrated in FIG. 3C), which may be used to perform any one, any combination, or all of the following functions: control the magnetic field circuitry; analyze the sensor output generated by the magnetic sensor; or sort cells of interest. Magnetic field circuitry is one example of a magnetic field generator that may be controlled by an analytics/sorting system 360. In particular, responsive to control signals from the analytics/sorting system 360, the magnetic field circuitry 352 may generate magnetic fields (e.g., by controlling the frequency and/or amplitude of an AC current) to generate the magnetic fields. In the instance that the sensor 356 is a magnetic sensor, the magnetic sensor may generate sensor output (e.g., magnetic sensor data) that is transmitted to the analytics system. Magnetic sensor is one example of a type of sensor 356 that is configured to generate sensor data. Another example of a type of sensor 356 that is configured to generate sensor data is an optical sensor (e.g., a camera or other imaging device) that is configured to generate optical sensor data.

Analytics/sorting system 360 may obtain sensor data in one of several ways. In a first way, analytics/sorting system 360 may command sensor 356 to generate sensor data. In particular, analytics/sorting system 360 may command sensor 356 to generate sensor data timed based on when analytics/sorting system 360 controls the magnetic field circuitry 352 (e.g., timed such that a predetermined time after controlling the magnetic field circuitry 352, the analytics/sorting system 360 commands the sensor 356 to generate sensor data). As one example, analytics/sorting system 360 may command sensor 356 to generate sensor data prior to analytics/sorting system 360 commanding magnetic field circuitry 352 generating a magnetic field. After analytics/sorting system 360 commands magnetic field circuitry 352 to generate the magnetic field, analytics/sorting system 360 may command sensor 356 to generate sensor data. Analytics/sorting system 360 may, upon receipt of the sensor data from sensor 356, store the sensor data in a memory. In this way, analytics/sorting system 360 may obtain sensor data prior to and after application of the magnetic field. As another example, analytics/sorting system 360 may command sensor 356 to generate sensor data after a first command to magnetic field circuitry 352, thereby generating a first magnetic field, and then after a second command to magnetic field circuitry 352, thereby generating a second magnetic field, with the first magnetic field being different from the second magnetic field.

In the first way and in the instance that sensor 356 is an optical sensor, analytics/sorting system 360 may control the optical sensor in order for the optical sensor to generate the optical sensor data indicative of the movement of the magnetic bead labeled to the target cell based on the control of the magnetic field generator (e.g., prior to generating the magnetic field, after generating the first magnetic field but before generating the second magnetic field, or after generating the second magnetic field).

In the first way and in the instance that sensor 356 is a magnetic sensor, analytics/sorting system 360 may control the magnetic sensor in order for the optical sensor to generate the optical sensor data indicative of the movement of the magnetic bead labeled to the target cell based on the control of the magnetic field generator (e.g., prior to generating the magnetic field, after generating the first magnetic field but before generating the second magnetic field, or after generating the second magnetic field).

In a second way, sensor 356 may periodically send sensor data to analytics/sorting system 360 (without previously being prompted by a command from analytics/sorting system 360). In this implementation, analytics/sorting system 360 may save the sensor data based on the timing of generating the magnetic field (e.g., prior to generating the magnetic field, after generating the first magnetic field but before generating the second magnetic field, or after generating the second magnetic field).

In the second way and in the instance that sensor 356 is an optical sensor, analytics/sorting system 360 may control saving the optical sensor data, indicative of the movement of the magnetic bead labeled to the target cell based on the control of the magnetic field generator, depending on generating the magnetic field (e.g., prior to generating the magnetic field, after generating the first magnetic field but before generating the second magnetic field, or after generating the second magnetic field).

In the second way and in the instance that sensor 356 is a magnetic sensor, analytics/sorting system 360 may control saving the magnetic sensor data, indicative of the movement of the magnetic bead labeled to the target cell based on the control of the magnetic field generator, depending on generating the magnetic field (e.g., prior to generating the magnetic field, after generating the first magnetic field but before generating the second magnetic field, or after generating the second magnetic field).

Regardless of the way in which the sensor data is stored, analytics/sorting system 360 may analyze the stored sensor data in order to determine whether the sensor data is indicative of movement, responsive to the generated magnetic field, of the magnetic bead labeled to the target cell. In the instance that the sensor data is optical data, analytics/sorting system 360 may analyze the optical data (e.g., a series of images) to determine whether there was movement in the magnetic bead labeled to the target cell. Specifically, analytics/sorting system 360 may perform image analysis on a first image to identify a first plurality of objects in the first image. Specifically, the image analysis may identify in the first image the magnetic bead labeled to the target cell (e.g., based on size of the magnetic bead labeled to the target cell). Analytics/sorting system 360 may perform image analysis on a second image to identify a second plurality of objects in the second image. Again, the image analysis may identify the magnetic bead labeled to the target cell in the second image. Analytics/sorting system 360 may then correlate the objects in the first plurality of objects with the objects the second plurality of objects to determine whether one, some, or all of the first plurality of objects have moved (e.g., identify coordinates of the identified magnetic bead labeled to the target cell(s) in the first plurality of objects with the coordinates of the of the identified magnetic bead labeled to the target cell(s) in the second plurality of objects to determine whether the coordinates for a respective object in the first plurality of objects are the same as the coordinates for the respective object in the second plurality of objects).

In the instance that the sensor data is magnetic data, analytics/sorting system 360 may analyze the magnetic data to determine whether there was movement in the magnetic bead labeled to the target cell. Specifically, the magnetic data may comprise a map of the magnetic objects in the well. Analytics/sorting system 360 may compare a first map of the magnetic objects (from first magnetic data) with a second map of the magnetic objects (from second magnetic data, which is obtained after a magnetic field is applied). The comparison of the first map with the second map may then be used to determine whether there was movement in the magnetic bead labeled to the target cell. For example, analytics/sorting system 360 may specifically identify coordinates, based on size, the magnetic bead labeled to the target cell in the first map, identify coordinates, based on size, the magnetic bead labeled to the target cell in the second map, and compare the different identified coordinates to determine whether the magnetic bead labeled to the target cell has moved. As another example, analytics/sorting system 360 may identify all of the particles that have moved based on a comparison of the first map and the second map, and for particles that are identified as moved, determine (e.g., based on size) whether the moved particle is a magnetic bead labeled to the target cell.

Figure 3C:
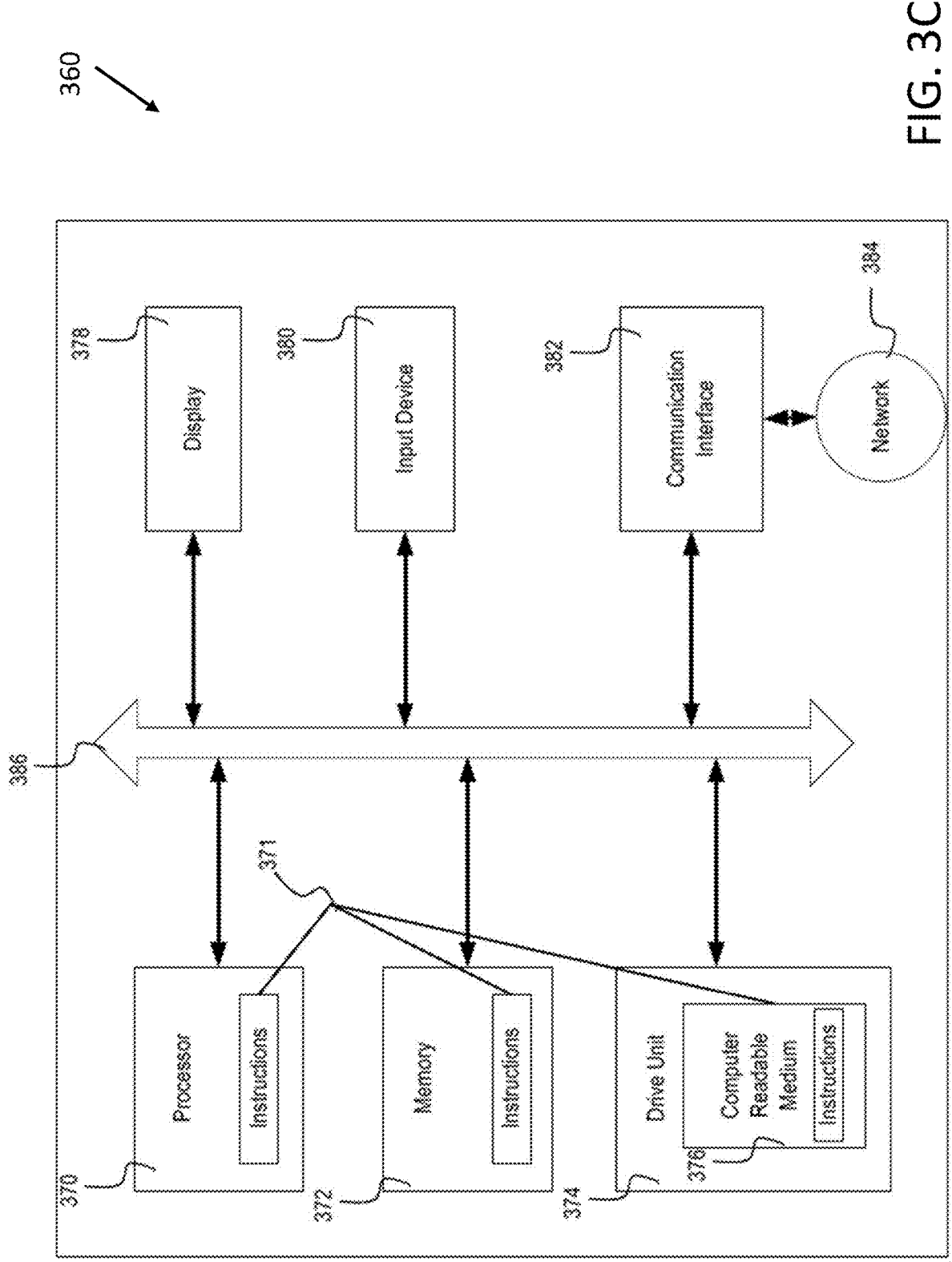
FIG. 3C illustrates an analytics system.

FIG. 3C illustrates one example of analytics/sorting system 360. In one implementation, analytics/sorting system 360 may comprises a computer system. For example, analytics/sorting system 360 may include an ordered listing of a set of instructions 371 that may be executed to cause the analytics/sorting system 360 to perform any one or more of the methods or computer-based functions disclosed herein, such as to analyze and/or sort the cells. Further, the analytics/sorting system 360 may comprise a single computer or multiple computers. Analytics/sorting system 360 may operate as a stand-alone device or may be connected, e.g., using the network 384, to other computer systems or peripheral devices, such as to enrichment system 262 and single cell identification and sorting 264. Further, the block diagram in FIG. 3C may similarly be used for enrichment system 262 and single cell identification and sorting 264. In this regard, any discussion below regarding analytics/sorting system 360 may be applied to enrichment system 262 and single cell identification and sorting 264.

In a networked deployment, analytics/sorting system 360 may operate in the capacity of a server or as a client-user computer in a server-client user network environment, or as a peer computer system in a peer-to-peer (or distributed) network environment. Analytics/sorting system 360 may also be implemented as or incorporated into various devices, such as a personal computer or a mobile computing device capable of executing a set of instructions 371 that specify actions to be taken by that machine. Further, each of the systems described may include any collection of sub-systems that individually or jointly execute a set, or multiple sets, of instructions to perform one or more computer functions. As discussed herein, the instructions may be manifested in logic.

Analytics/sorting system 360 may include a memory 372 on a bus 386 for communicating information. Code operable to cause the computer system to perform any of the acts or operations described herein may be stored in the memory 372. The memory 372 may be a random-access memory, read-only memory, programmable memory, hard disk drive or any other type of volatile or non-volatile memory or storage device.

Analytics/sorting system 360 may include a processor 370, such as a central processing unit (CPU) and/or a graphics processing unit (GPU). The processor 370 is one example of a controller (such as a digital controller) and may include one or more general processors, digital signal processors, application specific integrated circuits, field programmable gate arrays, digital circuits, optical circuits, analog circuits, combinations thereof, or other now known or later-developed devices for analyzing and processing data. The processor 370 may implement the set of instructions 371 or other software program, such as manually-programmed or computer-generated code for implementing logical functions. The logical function or any system element described may, among other functions, process and/or convert an analog data source such as an analog electrical, audio, or video signal, or a combination thereof, to a digital data source for audio-visual purposes or other digital processing purposes such as for compatibility for computer processing.

Analytics/sorting system 360 may also include a disk or optical drive unit 374. The disk drive unit 374 may include a computer-readable medium 376 in which one or more sets of instructions 371, e.g., software, can be embedded. Further, the instructions 371 may perform one or more of the operations as described herein. The instructions 371 may reside completely, or at least partially, within the memory 372 and/or within the processor 370 during execution by analytics/sorting system 360. Accordingly, the databases may be stored in the memory 372 and/or the disk unit 374.

The memory 372 and the processor 370 also may include computer-readable media as discussed above. A "computer-readable medium," "computer-readable storage medium," "machine readable medium," "propagated-signal medium," and/or "signal-bearing medium" may include any device that includes, stores, communicates, propagates, or transports software for use by or in connection with an instruction executable system, apparatus, or device. The machine-readable medium may selectively be, but not limited to, an electronic, magnetic, optical, electromagnetic, infrared, or semiconductor system, apparatus, device, or propagation medium.

Additionally, analytics/sorting system 360 may include an input device 380, such as a keyboard or mouse, configured for a user to interact with any of the components of analytics/sorting system 360. In this way, an operator may control the processing of the blood sample. It may further include a display 378, such as a liquid crystal display (LCD), a cathode ray tube (CRT), or any other display suitable for conveying information. The display may act as an interface for the user to see the functioning of the processor 370, or specifically as an interface with the software stored in the memory 372 or the drive unit 374. As discussed above, the customer-controlled device may include a display and an input device, such as input device 380.

Analytics/sorting system 360 may include a communication interface 382 that enables communications via the communications network 384. The network 384 may include wired networks, wireless networks, or combinations thereof. The communication interface 382 network may enable communications via any number of communication standards, such as 802.11, 802.17, 802.20, WiMAX, 802.15.4, cellular telephone standards, or other communication standards, as discussed above. Merely because one of these standards is listed does not mean any one is preferred as any number of these standards may never actually be adopted in a commercial product.

Block diagrams of different aspects of the system may be implemented using the computer functionality disclosed in flow diagrams disclosed herein. Further, the flow diagrams may use computer readable instructions that are executed by one or more processors in order to implement the functionality disclosed. Finally, the displays may be output on an I/O device.

The present disclosure contemplates a computer-readable medium that includes instructions or receives and executes instructions responsive to a propagated signal, so that a device connected to a network may communicate voice, video, audio, images or any other data over the network. Further, the instructions may be transmitted or received over the network via a communication interface. The communication interface may be a part of the processor or may be a separate component. The communication interface may be created in software or may be a physical connection in hardware. The communication interface may be configured to connect with a network, external media, the display, or any other components in system, or combinations thereof. The connection with the network may be a physical connection, such as a wired Ethernet connection or may be established wirelessly as discussed below. In the case of a service provider server, the service provider server may communicate with users through the communication interface.

The computer-readable medium may be a single medium, or the computer-readable medium may be a single medium or multiple media, such as a centralized or distributed database, and/or associated caches and servers that store one or more sets of instructions. The term "computer-readable medium" may also include any medium that may be capable of storing, encoding or carrying a set of instructions for execution by a processor or that may cause a computer system to perform any one or more of the methods or operations disclosed herein.

The computer-readable medium may include a solid-state memory such as a memory card or other package that houses one or more non-volatile read-only memories. The computer-readable medium also may be a random access memory or other volatile re-writable memory. Additionally, the computer-readable medium may include a magneto-optical or optical medium, such as a disk or tapes or other storage device to capture carrier wave signals such as a signal communicated over a transmission medium. A digital file attachment to an email or other self-contained information archive or set of archives may be considered a distribution medium that may be a tangible storage medium. The computer-readable medium is preferably a tangible and non-transitory storage medium. Accordingly, the disclosure may be considered to include any one or more of a computer-readable medium or a distribution medium and other equivalents and successor media, in which data or instructions may be stored.

Alternatively or in addition, dedicated hardware implementations, such as application specific integrated circuits, programmable logic arrays and other hardware devices, may be constructed to implement one or more of the methods described herein. Applications that may include the apparatus and systems of various embodiments may broadly include a variety of electronic and computer systems. One or more embodiments described herein may implement functions using two or more specific interconnected hardware modules or devices with related control and data signals that may be communicated between and through the modules, or as portions of an application-specific integrated circuit. Accordingly, the present system may encompass software, firmware, and hardware implementations.

The magnetic sensor may be based on Hall-effect in current-carrying conductors implemented in the active layer of standard CMOS process. This is illustrated in FIGS.

Figure 4A:
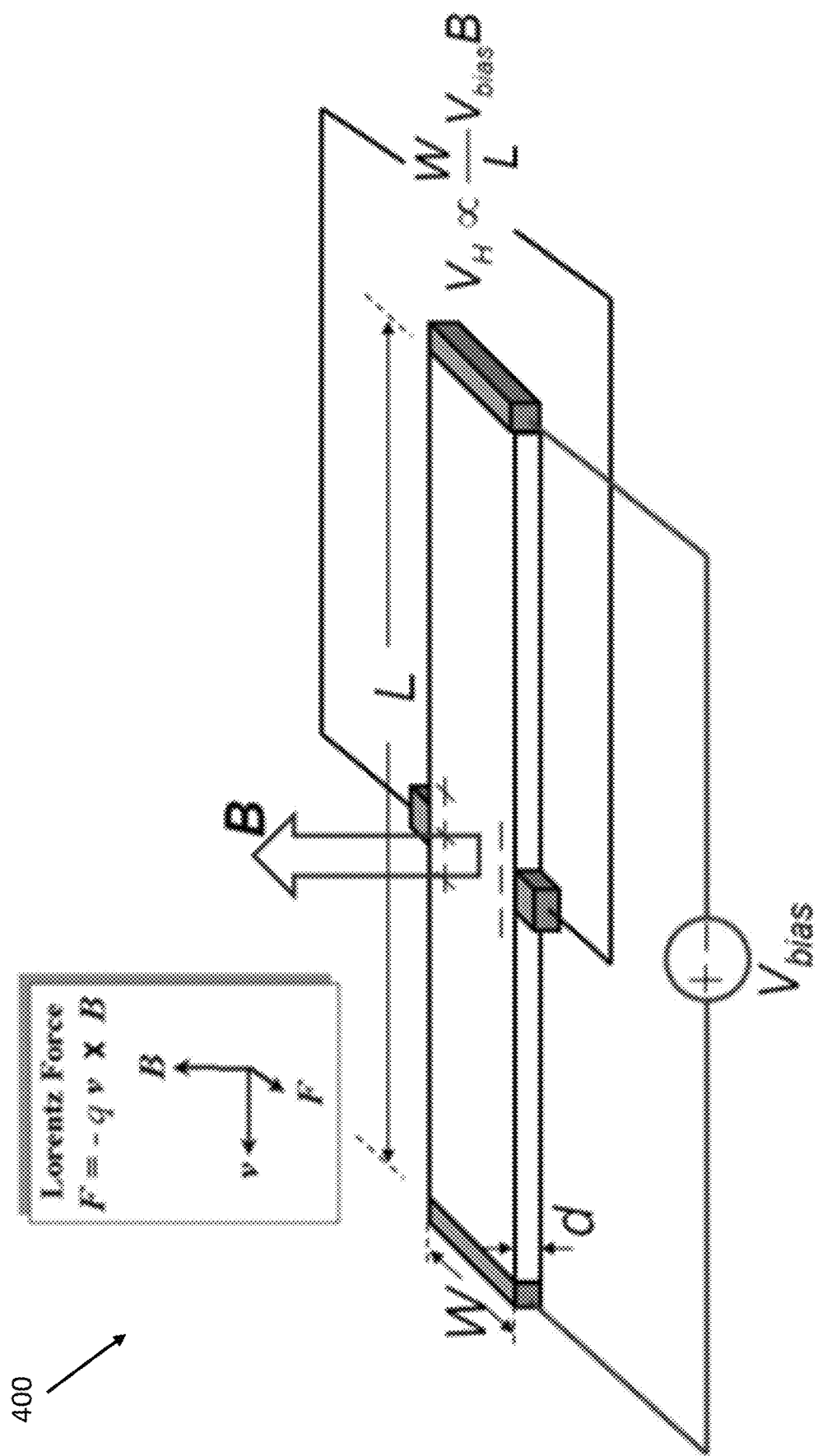
FIG. 4A is illustrates a Hall-effect sensor principle and implementation in CMOS process.
Figure 4B:
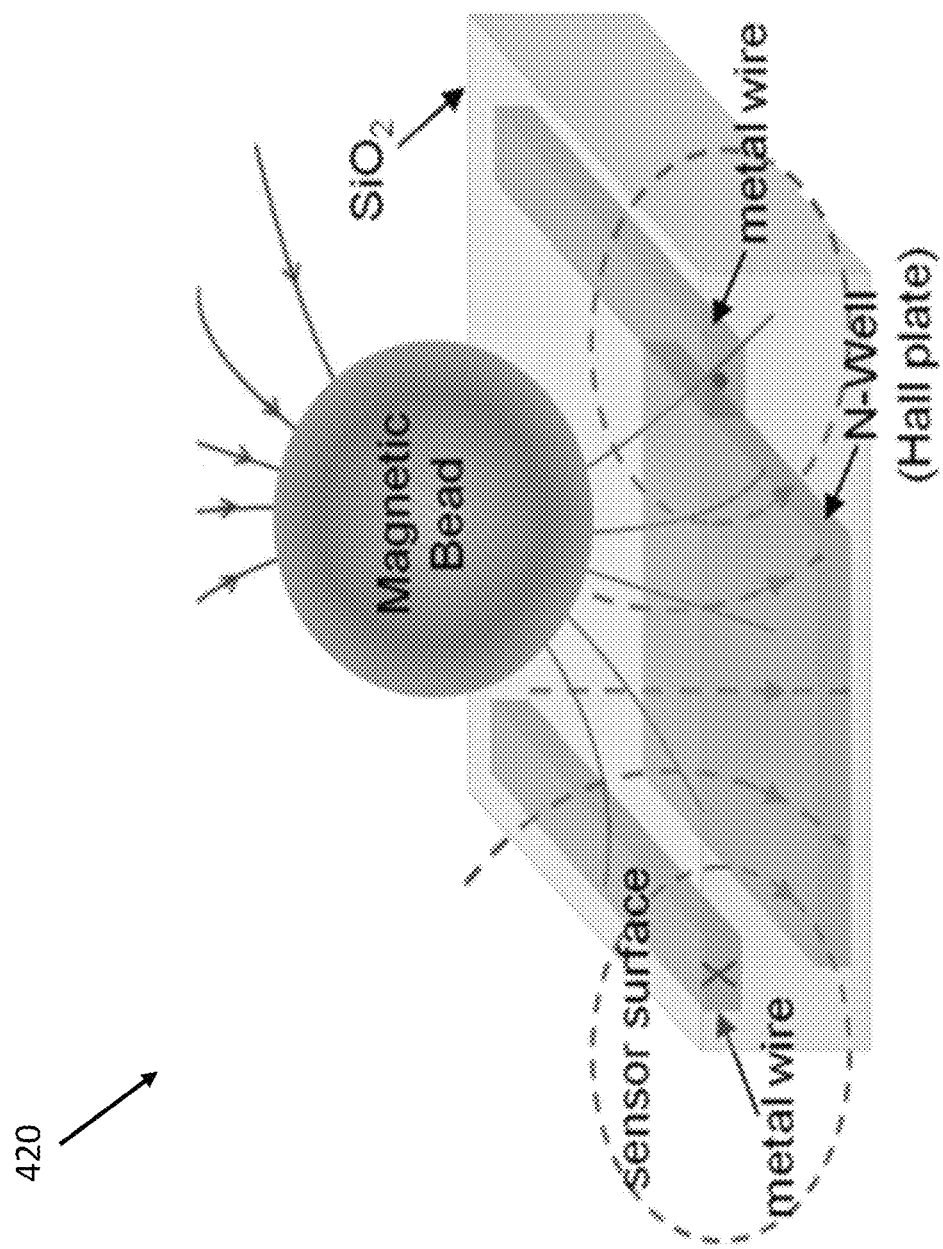
FIG. 4B includes a diagram illustrating the principle of detecting a bead on a CMOS Hall sensor surface.

4A-B. In particular, FIG. 4A illustrates in 400 a Hall-effect sensor principle and implementation in CMOS process. For a current-carrying conductor plate in a magnetic field transverse to the current direction, Lorentz force causes the charges to move along a curve path and therefore a Hall voltage that is proportional to the external magnetic field to develop across the plate. FIG. 4B includes a diagram 420 illustrating the principle of detecting a bead on a CMOS Hall sensor surface. The current-carrying metal wires, which may be covered with silicon oxide and may only be 1 μm from sensor surface, generate the magnetizing field (dashed lines) to magnetize the bead (solid lines). The magnetic fields are detected by the embedded Hall plate, which is implemented in the N-well layer of standard CMOS process. The current contacts and sensing contacts of the Hall plate are not shown.

In the depictions, each unit sensor occupies 5 μm×5 μm, which is close to the size of the bead labels. However, as discussed above, the area of the magnetic sensor may be more than one order of magnitude greater than the size of the bead labels (such as at least two orders of magnitude greater).

Figure 4C:
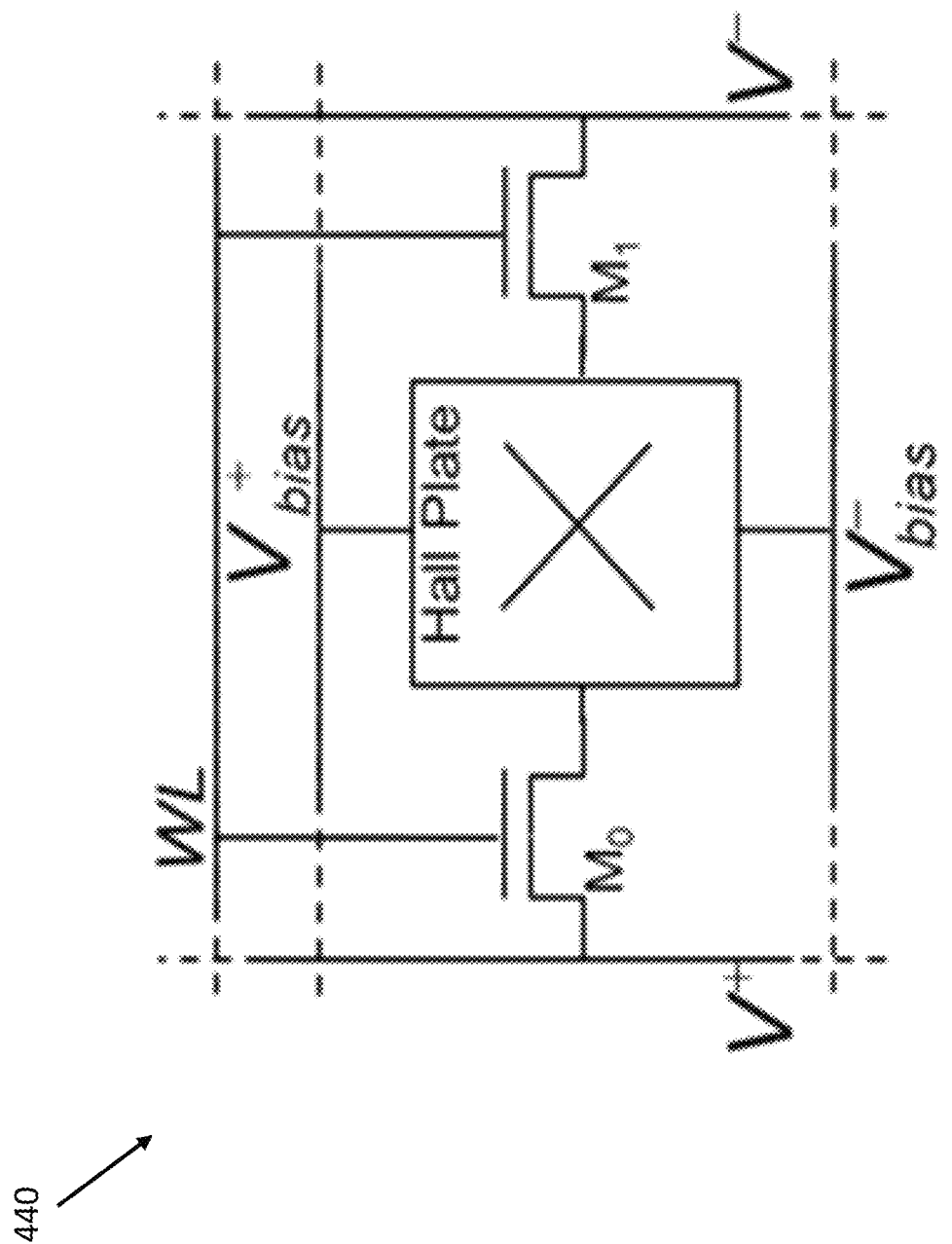
FIGS. 4C-D illustrate individual unit sensors, with FIG. 4C illustrating a schematic and FIG. 4D illustrating the layout, with both arranged in an 8×6 array.
Figure 4D:
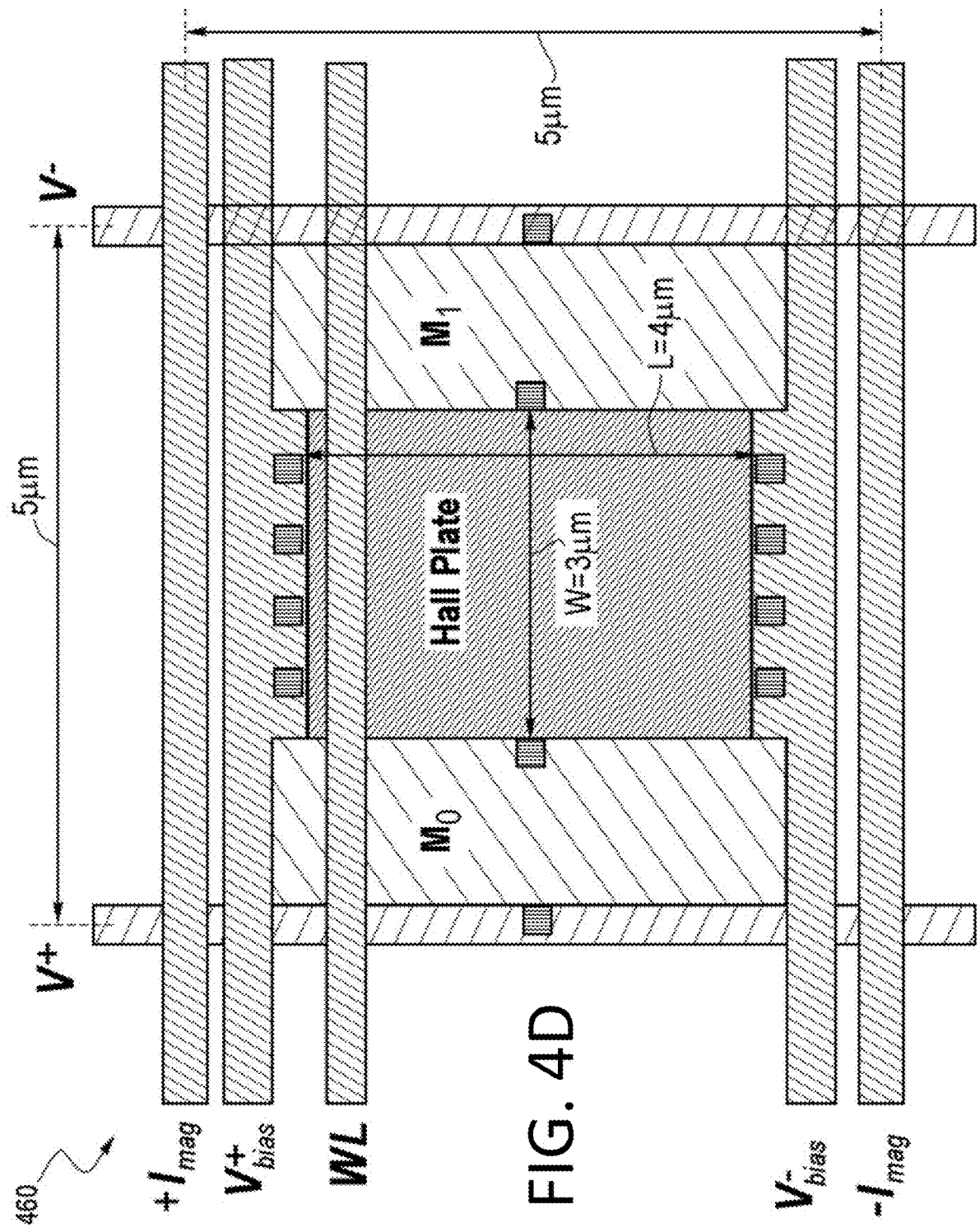

A Hall sensor array may then be implemented to detect the presence of any magnetic bead on its surface (FIGS. 4C-D). In particular, FIGS. 4C-D illustrate individual unit sensors, with FIG. 4C illustrating a schematic 440 (including transistors $M_0$ and $M_1$ activated by wordline WL, and Hall Plate biased by $V_{bias}$) and FIG. 4D illustrating the layout 460, with both arranged in an 8×6 array. By taking advantage of the high functionality of modern microelectronics, all three components for bead detection (sensors, magnets and readout circuits) may be integrated on a single 2.5 mm×2.5 mm CMOS chip, reducing system cost and ensuring device performance consistency.

Figure 4E:
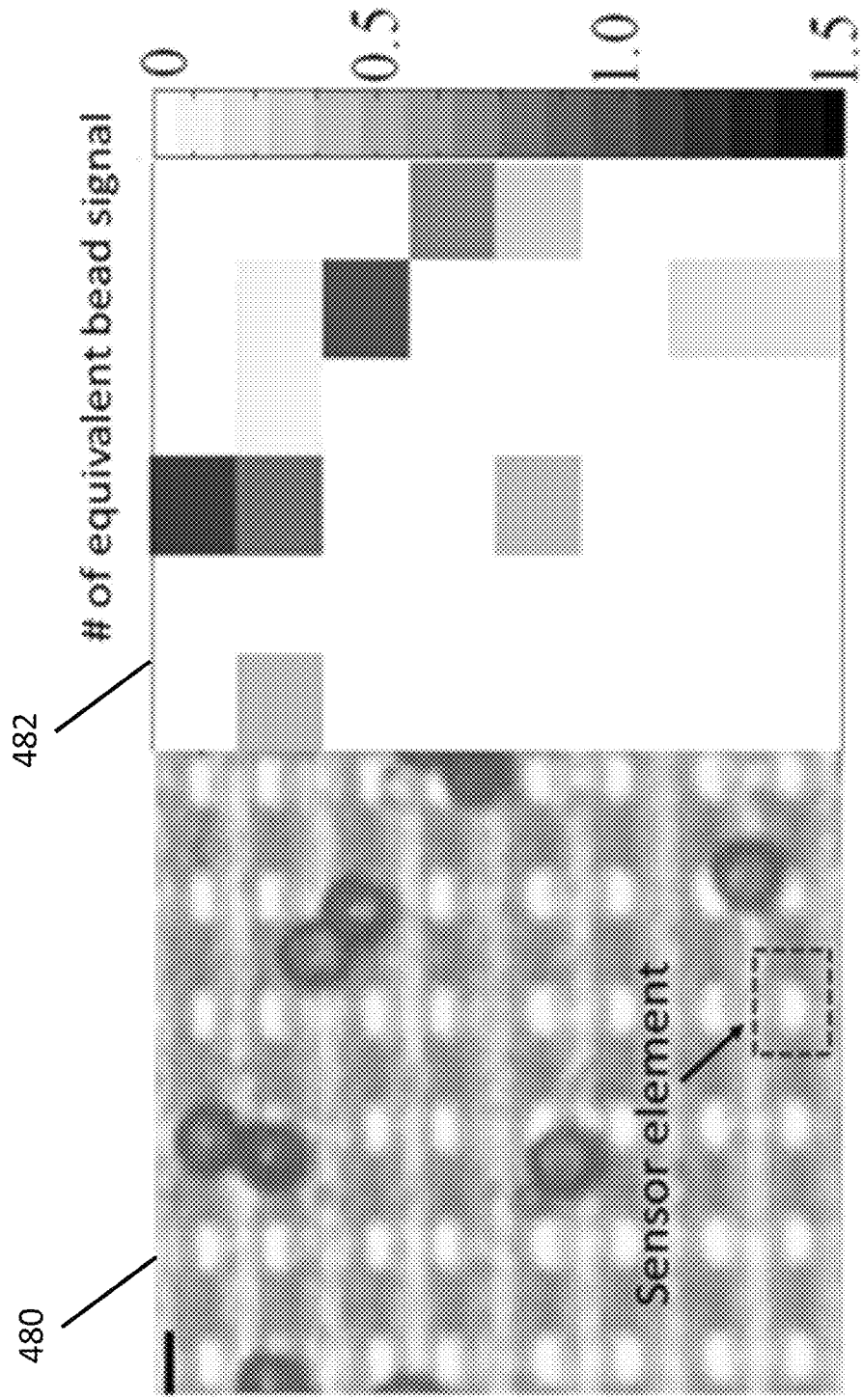
FIG. 4E illustrates on the left side a top view with detected beads and on the right side the output of the sensor array.

Single 4.5-μm microbeads may be detected anywhere on sensor array surface, with the sensor outputs correlating well with the image taken under optical microscope (see the left side 480 of FIG. 4E). Each unit sensor may comprise a Hall plate and two access transistors controlled by wordline (WL). Each wordline may be shared by sensors in the same row. Therefore, Hall sensor outputs (V+ & V−) in each row may be read out in parallel. FIG. 4E on the right side 482 is the output of the sensor array, demonstrating the bead signal detected by an 8×6 sensor array on the CMOS chip. A 2-μl droplet of diluted Dynabeads M450 (4.5 μm diameter) bead sample was placed on the sensor surface and left to air dry (illustrated on the left). This optical image illustrated on the left side of FIG. 4E matches the output of the 48-sensor array (with a scale bar of 5 μm) shown on the right. As shown, the sensor signal is strongest when the bead is located at the middle of a sensor; when the bead is located on the border of sensors, it is detected by multiple adjacent sensors with weaker signal.

Figure 4F:
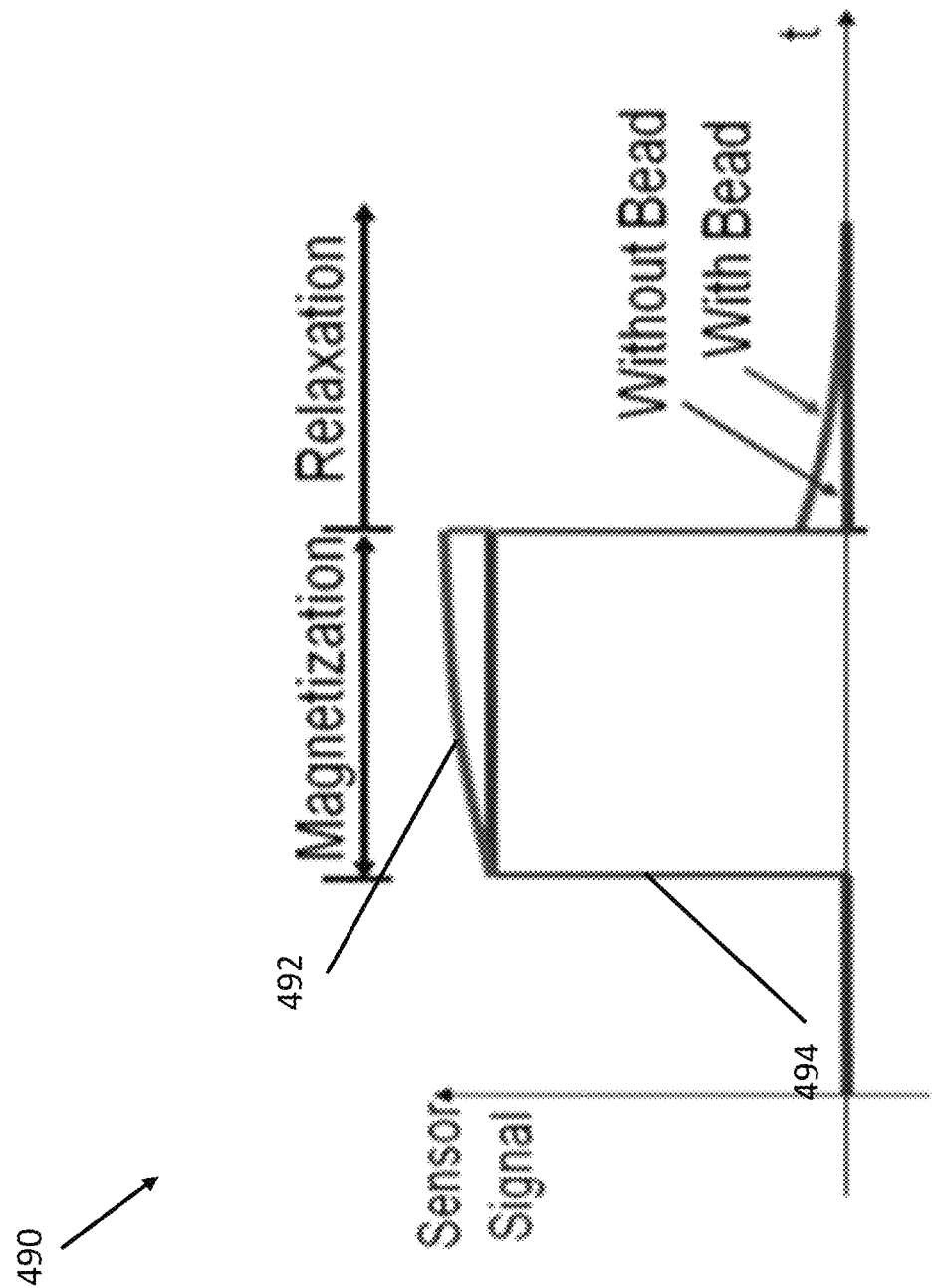
FIG. 4F illustrates principles of bead detection by relaxation.
Figure 4G:
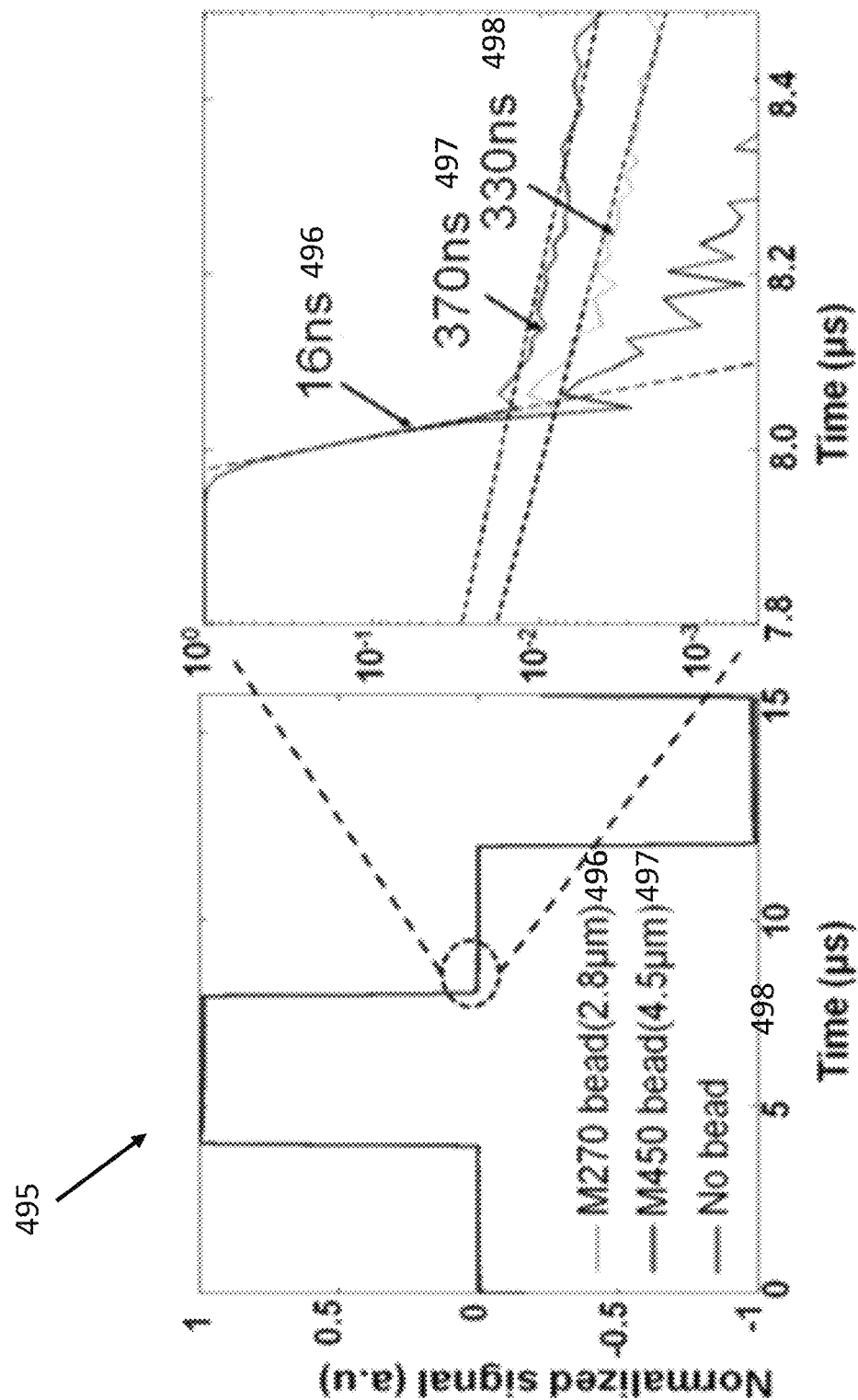
FIG. 4G illustrates detection of single bead using the magnetic relaxation method.

Robust detection of single bead may be achieved by adopting a method based on the magnetic relaxation of the magnetic bead (illustrated in FIGS. 4F-G). In particular, FIG. 4F illustrates a FIG. 490 of principles of bead detection by relaxation. The sensor may respond when a bead is present (curved line 492) or absent (straight line 494) are shown. In the present disclosed relaxation method, the bead signal is measured during relaxation when the large magnetizing field is off for robustness and to reduce detection errors. FIG. 4G illustrates detection of single bead using the magnetic relaxation method. Single 4.5-μm (Dynabeads M450 (497)), 2.8-μm (M270 (496)) beads and no bead (498) are tested with same sensor. The bead is magnetized by an external field with a 4-phase modulation repeated by many cycles. The averaged signal is recorded and then normalized (shown on the left of FIG. 4G). An expanded view on the right of FIG. 4G illustrates the bead relaxation traces in semilog-scale where the beads' exponential decay with a time constant ~300 ns may be easily recognized.

Detecting a superparamagnetic bead includes magnetizing the bead first. However, during the magnetization, the bead's field is eclipsed by the magnetizing field which is usually several orders of magnitude larger. Therefore, conventional methods suffer from detection errors that could lead to false positives and negatives. In one implementation, single bead detection is based on measuring the Néel relaxation of the bead (see FIG. 4F). When the magnetizing field is turned off abruptly, the beads signal will decay to zero following its Néel relaxation time constant, described by the Néel-Brown model. Since the bead signal is measured during relaxation where the interfering magnetizing field goes to zero, detection errors are significantly reduced. The implemented bead detection sequences comprises 4 phases of magnetizing field modulation by controlling the current through the metal wires (electromagnets). With this modulation sequence, net DC magnetizing field during a cycle remains at zero. The modulation sequence repeats for several cycles and the recorded sensor signal may be averaged to reduce white noise. A correlated double sampling algorithm is then applied to reject sensor offset and other non-idealities to achieve high signal-to-noise ratio.

Figure 5A:
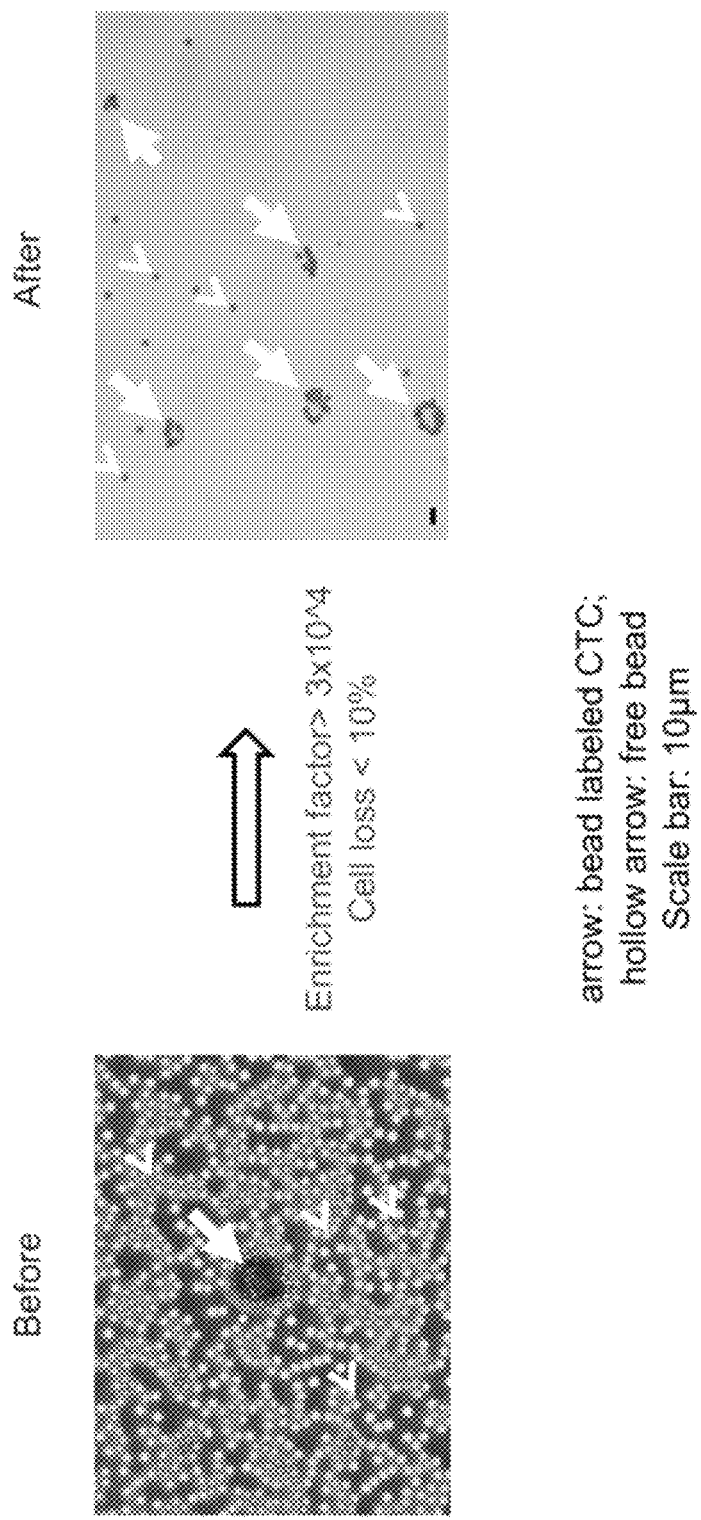
FIG. 5A illustrates one example of free bead removal.

FIG. 5A illustrates one example of free bead removal, illustrating the free beads in the solution before removal of at least some of the free beads, and after applying a free bead removal/reduction step. As discussed above, one of multiple methods of removal or reduction of free beads may be used, including membrane filtration and density gradient centrifugation. As discussed above, free beads and bead-bound cells are very different in size (4.5 μm vs. 20 μm) and density (1.6 g/cm3 vs. 1.3 g/cm3 for a 20-μm target cell fully conjugated with beads). In this regard, membrane filtration or density gradient centrifugation may be used in order to achieve an enrichment factor over $3 \times 10^4$ and with target cell loss less than 10% (see FIG. 5A). Thus, as shown, many free beads are removed (such as reducing by an order of magnitude, or reducing by multiple orders of magnitude), while reducing the cells by less than 10% (e.g., reducing the cells by much less than an order of magnitude).

As discussed above, in one implementation, the system may reduce the number of free beads in the fluid, such as in the blood sample. Magnetic beads may be applied to the fluid (such as to a blood sample) in the cell isolation step. A large majority of the magnetic beads may not bind, leaving many of the beads to be unattached (e.g., free beads). Optionally, after applying the unbound beads to the fluid, the system may perform one or more steps in order to reduce the number of free beads in the fluid.

The number of free beads may be reduced in one of several ways. In one way, a filter may be used to remove some of the free beads from the fluid. As discussed above, the free beads may be smaller than the CTCs that have a magnetic bead bound thereto. For example, the free beads may be less than 5 μm, such as 4.5 μm, whereas the CTCs may be on the order of 20 μm. Further, other cells, such as white blood cells, may be approximately 10 μm. Thus, in one implementation, a filter, such as a filter membrane, which may pass particles less than 7 μm, may be used. Specifically, the fluid may be passed through the filter membrane, which has a mesh such that particles less than 7 μm, are passed through. In this way, cells larger than 7 μm, such as CTCs or white blood cells, may be caught in the filter membrane, whereas free beads may pass through the filter membrane. Alternatively, a filter membrane with a mesh that catches particles greater than 12 µm may be used.

For example, for membrane filtering, the following filter may be used: 13 mm, 7-µm pores, Precision Membrane, Provo, Utah. For density gradient centrifugation, the following parameters may be used: Ludox TM-50, 1.4 g/cm$^3$, W.R. Grace Inc, Columbia, Md. In both examples, free beads may be reduced to several hundreds.

In this case, CTCs may be caught in the filter membrane, whereas free beads and white blood cells may pass through. In this way, the number of free beads in the fluid may be reduced.

In another way, a centrifuge may be used to reduce the number of free beads in the fluid. For example, the density of the free beads may be more than the density of the CTCs that have a magnetic bead bound thereto. Thus, a centrifuge may be used to spin the fluid, thereby separating particles at different densities, such as separating the free beads from the CTCs that have a magnetic bead bound thereto.

In still another way, one or more electric currents may be used to separate the free beads from other particles (such as CTCs that have a magnetic bead bound thereto) in the fluid. For example, the weight of the free beads is less than the weight of the CTCs that have a magnetic bead bound thereto. Thus, a current may be applied that is sufficient to move a free bead, but insufficient to move CTCs that have a magnetic bead bound thereto. In this way, the current may be used to move the free beads within the fluid. After which, the free beads may be removed from the fluid.

FIG. 5B illustrates one example of on-chip bead manipulation (with a scale bar of 10 µm). By programming the currents flowing through each metal wire, the chip may generate spatially-patterned microscopic magnetic field on the chip surface and transport individual bead-bound cells to desired locations. For instance, bovine capillary endothelial (BCE) cells engulfed with magnetic particles may be manipulated with on-chip microcoils.

Thus, in one implementation, the chip may include 256 metal wires and controlling circuits to manipulate movement of the magnetic beads (FIG. 4B). In this regard, the generated magnetic field may be used to attract the beads towards local peak field position. For example, beads may move at a speed of 16 µm/s with 20 mA switching. The metal wires of the chip may be designed using modeling of bead movement with multi-physics software COMSOL (COMSOL Inc., Burlington, Mass.) by calculating magnetic force, Stoke's drag force and chip surface friction force. Each wire in FIG. 5B is 2 µm in width and 2 mm in length. Metal wire pitch is 8 µm. In the implementation of FIG. 5B, a droplet of 4.5-µm beads (CELLection® biotin binder, Invitrogen, Carlsbad, Calif.) was added to chip surface. A 20 mA current is then switched into the metal wires from left to right. The beads move at a speed of 16 µm/s. Specifically, FIG. 5B illustrates at different times (t=1 second; t=2 seconds; t=4 seconds) the effect on the beads with applying a magnetic field via metal wires. Arrowheads in FIG. 5B illustrates metal wires, whereas arrows represent reference points.

Thus, in one implementation, prior to the cell sorting step, the number of non-CTC cells may be reduced. For example, the number of white blood cells may be reduced by an order of magnitude or by several orders of magnitude, such as via the cell isolation step. After which, the number of white blood cells may be comparable with the number of CTCs (e.g., on the same order of magnitude). As another example, the number of free beads may be reduced by an order of magnitude or by several orders of magnitude, such as via the free bead reduction step.

After the number of non-CTC cells may be reduced, the fluid may be inserted into the well. The system may insert the fluid into the well in one of several ways. In one way, the system may pipet the fluid into the well, such as via a syringe pump. In another way, the system may use microfluidics to introduce the fluid into the well. As one example, the microfluidics may include one or more channels to guide fluid to and/or from the well.

In one implementation, the microfluidic channel, with inlet and outlet ports, may connect to the sample well so that after the target cells are sorted, the non-target cells and contaminants may be washed off from the well surface (e.g., the bottom surface and/or sides of the well) so the sensor device can be reused. In an alternate implementation, each corner (e.g., each reservoir) of the chip may be connected with a microfluidic channel, with inlet and outlet ports, so that the sorted single target cell (e.g., located at the reservoir of the sample well) may be transferred to a vial or tube or micro-well for further analysis. The number of inlet (or outlet) ports may be one or more than one (in order to mix fluids).

Figure 5C:
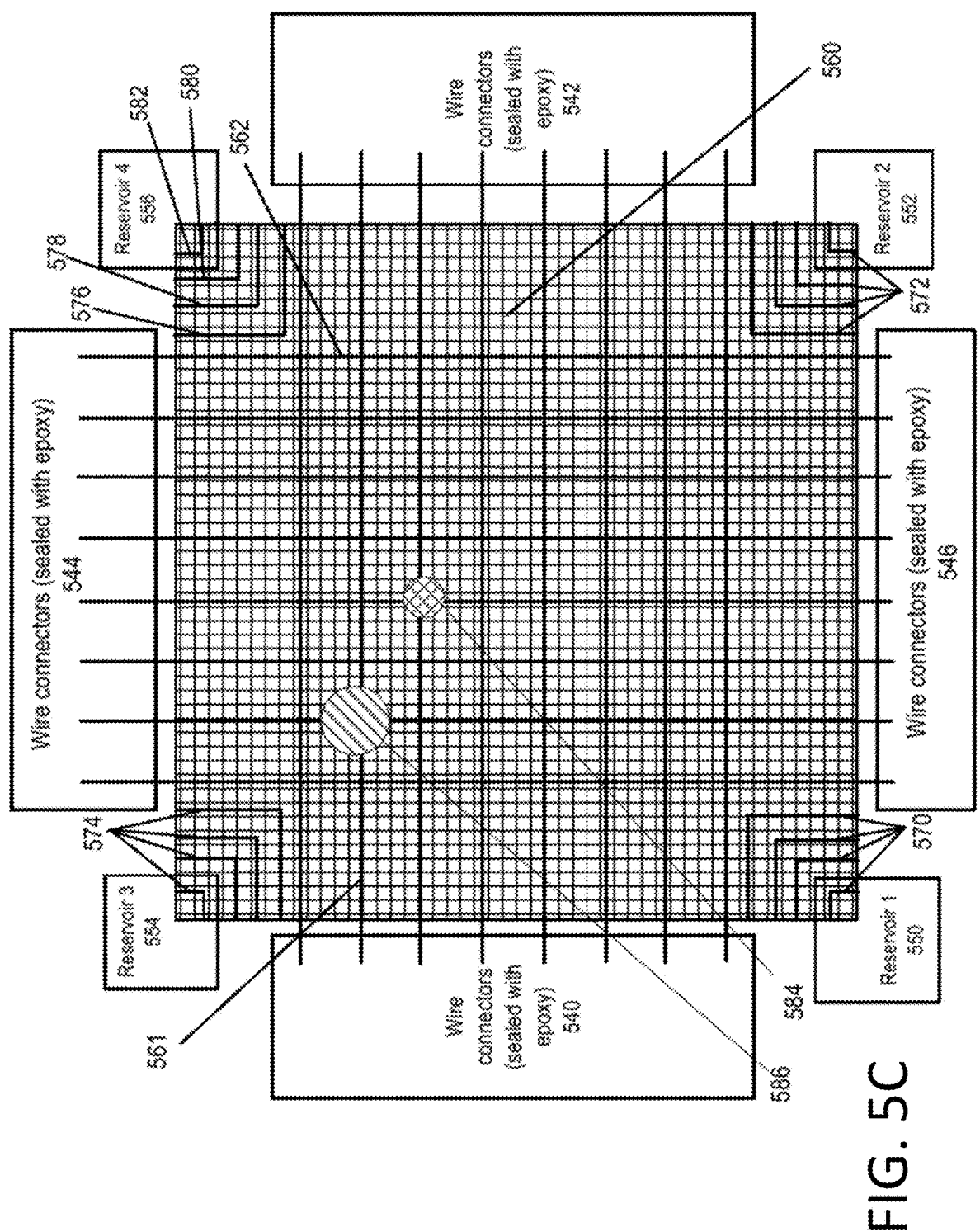
FIG. 5C illustrates a layout of a well and associated circuitry for cell identification and/or cell sorting.
Figure 5D:
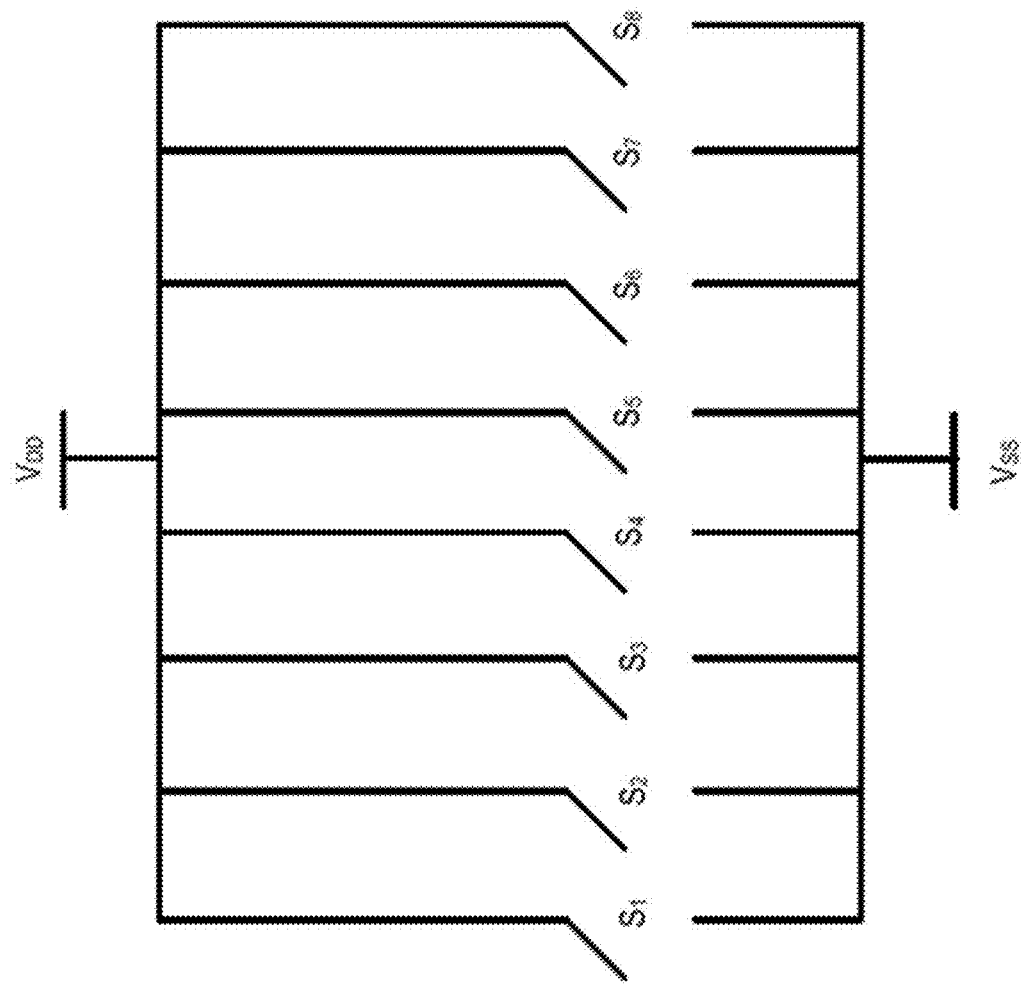
FIG. 5D illustrates control circuitry for the circuitry illustrated in FIG. 5C.
Figure 5D:
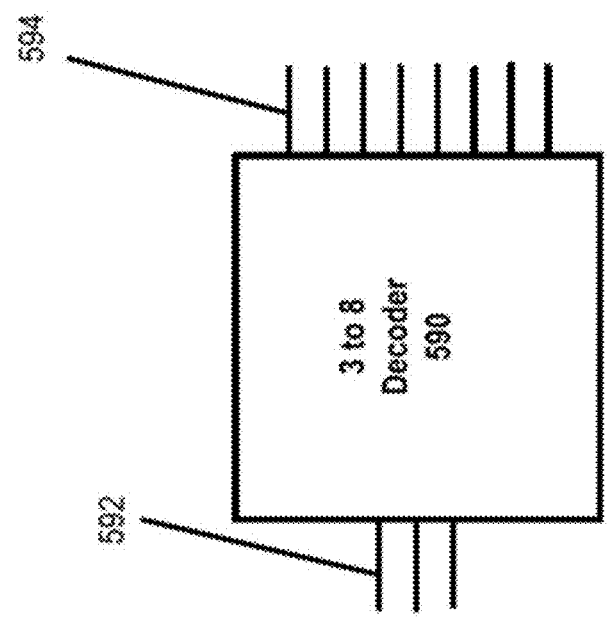

FIG. 5C illustrates a layout of a well and associated circuitry for cell identification and/or cell sorting. As discussed above, the fluid may be introduced into the well 560 (shown in a mesh background) in one of several ways. After introduction, the particles in the fluid may be subject to a magnetic field, such as generated by horizontal wires 561 (8 horizontal wires shown) and by vertical wires 562 (8 vertical wires shown). Horizontal wires 561 and vertical wires 562 may be positioned relative to a surface of the well (such as underneath a bottom of the well). The horizontal wires may be connected to wire connectors 540, 542, which may be sealed with epoxy. Likewise, the vertical wires may be connected to wire connectors 544, 546, which may be sealed with epoxy.

As shown in FIGS. 5D, 6, and 7A-B, metal lines are used to generate the magnetic field. Metal lines, as opposed to a coil, may provide better control over the movement of the beaded target cells. For example, if a photograph of the well is taken before and after application of the magnetic field, the system (or an operator) may make a better determination after turning on one of the metal lines. Further, one or more algorithms may be used to turn on/off the different wires in sequence in order to move the beaded target cells to a respective reservoir (as opposed to a coil, which does not offer as precise a control of the magnetic field).

One example of control current through the horizontal wires 561 and the vertical wires 562 is illustrated in FIG. 5E. In particular, inputs 592 to a decoder or other type of multiplexer (such as 3-to-8 decoder 590) may generate an output 594. The output may be used to control one of the switches, such as $S_1$, $S_2$, $S_3$, $S_4$, $S_5$, $S_6$, $S_7$, and $S_8$ (connected between $V_{DD}$ (e.g., 5V) and $V_{SS}$ (e.g., circuit ground) As one example, an input of 001 may translate into the output of decoder to close switch $S_2$, so that current flows through the respective wire.

The control of current through the wires may be accomplished by analytics/sorting system 360. For example, particles 584 and 586 may be in well 560. Analytics/sorting system 360 may control the current through the horizontal wires 561 and the vertical wires 562 on a quadrant by quadrant basis so that the magnetic particles may be moved to the reservoir in the respective quadrant. Specifically, analytics/sorting system 360 may control the current through the horizontal wires 561 and the vertical wires 562 so that magnetic particles in the lower left quadrant may be moved toward Reservoir 1 (550), in the lower right quadrant may be moved toward Reservoir 2 (552), in the upper left quadrant may be moved toward Reservoir 3 (554), and in the upper right quadrant may be moved toward Reservoir 4 (556). In this way, the analytics/sorting system 360 (such as the processor of the analytics/sorting system 360) may control the magnetic field to different parts of the well (e.g., control the timing of current flowing through the horizontal wires 561 and the vertical wires 562 in order to generate magnetic fields in different parts of the well at different times).

More specifically, analytics/sorting system 360 may control a multiplexer, which in turn controls switches to turn on/off current to the various wires. In one implementation, analytics/sorting system 360 may control the switches in a predetermined sequence (without any feedback from a sensor). In an alternate implementation, analytics/sorting system 360 may control the switches (which in turn controls the wires) based on sensor input. In a first specific implementation, the sensor input may comprise optical sensor input, whereby the optical sensor provides data to the analytics/sorting system 360, with the analytics/sorting system 360 determining movement of the beads. In a second specific implementation, the sensor input may comprise magnetic sensor input, whereby the magnetic sensor provides data to the analytics/sorting system 360, with the analytics/sorting system 360 determining movement of the beads. Thus, the sensor input may be used as feedback for the analytics/sorting system 360 to determine when/whether turn on the different wires in well 560.

After the magnetic particles are moved toward a respective reservoir, wires may bracket the reservoir, such as illustrated in wires 570 bracketing Reservoir 1 (550), wires 572 bracketing Reservoir 2 (552), and wires 574 bracketing Reservoir 3 (554). Further wires 576, 578, 580, 582 bracket Reservoir 4 (556). 570, 572, 574, 576, 578, 580, 582 may be positioned relative to a surface of the well (such as underneath the bottom of the well). The distance between wires 576 and 578 may be 5 µm (or on the order of 5 µm). Analytics/sorting system 360 may control the current through the different wires, such as 570, 572, 574, 576, 578, 580, 582 to guide the magnetic particles to the respective reservoir. For example, with regard to Reservoir 4 (556), analytics/sorting system 360 may first turn on wire 576, then wire 578, then wire 580, and then wire 582. This sequence may similarly be performed for wires 570, 572, 574. Thus, in one implementation, the magnetic particles may be guided to a respective reservoir solely by controlling the current through various wires. In an alternate implementation, the magnetic particles may be guided to a respective reservoir by controlling the current through various wires (in order to place the magnetic particle proximate to the respective reservoir), and thereafter using a magnetic gripper in order to place the magnetic particle into the reservoir (e.g., magnetic tip that is used to move the bead bound cell to the reservoir).

Thus, FIG. 5C illustrates one or more wires that are shaped or arranged based on the reservoir (such as shaped based on an edge of the reservoir). As one example, Reservoir 4 (556) is rectangular in shape. One, some or all of wires 576, 578, 580, 582 may be shaped or arranged such that they follow an edge (such as a corner of Reservoir 4 (556)).

Further, FIG. 5C illustrates different layouts of wires. For example, horizontal wires 561 and vertical wires 562 are arranged in a grid pattern, whereas wires 570, 572, 574, 576, 578, 580, 582 are arranged in a different pattern (such as based on the shape of the respective reservoir). In this way, the analytics/sorting system 360 may control the current through the different wires, and generate different magnetic fields. Specifically, a first magnetic field may be generated using horizontal wires 561 and vertical wires 562 in order to move the bead labeled target cell close to a respective reservoir, and a second magnetic field may be generated using wires 570, 572, 574, 576, 578, 580, 582 in order to guide the bead labeled target cell closer to (or into) the respective reservoir.

In one implementation, the sorted single cell in the reservoir may be transferred to another container, such as a tube or vial or micro-well, for further analysis. The transferal of the sorted single cell may be performed in one of several ways. In one way, the transfer may occur using a microfluidic channel. Alternatively, the transfer may occur using a magnetic fine tip. As one example, the magnetic fine tip may be manually controlled in order to transfer the single sorted single cell (with magnetic bead attached thereto) to the other container. Alternatively, the system may detect the single sorted single cell (with magnetic bead attached thereto). Responsive to the detection of the single sorted single cell (with magnetic bead attached thereto), the system may automatically control the magnetic fine tip in order to move the single sorted single cell (with magnetic bead attached thereto) to the other container.

For single cell sorting, the wires, such as horizontal wires 561 and vertical wires 562, may be designed to move bead bound cells, such as Caco-2 cells, at a certain rate (e.g., X µm/s). For example, the wires may be designed such that a 20-µm Caco-2 cell with 50% surface area conjugated with beads can move at 12 µm/s with 30 mA. In one implementation, the chip may be designed with a current magnitude that can be programmed from 10 mA to 60 mA. Since the magnetic force on a superparamagnetic particle (e.g., Dynabead) in a magnetic field is given by $F=V\Delta\chi(B\cdot\nabla)B/\mu_0$ where V is the particle's volume, $\Delta\chi$ is the difference in magnetic susceptibilities between the particle and the surrounding medium, $\mu_0$ is the vacuum permeability and B is the applied magnetic field generated by the metal wires which is proportional to the injected current as described in Ampere's Law. Therefore, the magnetic force is roughly proportional to the square of the injected current magnitude. In this regard, the isolated target cells may be manipulated with a speed more than 10 µm/s. One point of interest in the design of the layout of the wires may include an amount of time to move from one point of interest in the well to another, such as from the center of the chip to a corner (which may be on the order of ~3.5 mm), which may be the longest path a cell travels in the well. As discussed above, at the 4 corners of the chip, magnetic tips, such as 4 fine magnetic tips, may be used to pick a single bead-bound cell and place it in a respective reservoir.

In one implementation, the magnetic fields may be generated serially (e.g., the first magnetic field is generated first and the second magnetic field is generated thereafter without any overlap when the two magnetic fields are generated simultaneously). In an alternate implementation, the magnetic fields may be generated such that they overlap at least partly in time (e.g., the first magnetic field and the second magnetic field are generated at least partly simultaneously).

After guiding the magnetic particles into the respective reservoir, the well 560 may be flushed, and another sample of fluid may be inserted into the well 560 (such as via pipetting or microfluidics). In this way, the system may act as a production line, inserting a small volume of fluid (e.g., 1 microliter), process the fluid (e.g., cell isolation and single cell sorting), clean the well (e.g., introduce buffer into the well and then flush the buffer out), then introduce the next sample volume.

Alternatively, instead of performing a free bead removal step (such as discussed above), the fluid sample may be diluted (such as diluted by 1000 times). The diluted fluid may then be introduced into the well as part of a production line, with the beads bound to the CTCs being guided into the respective reservoir.

Figure 6:
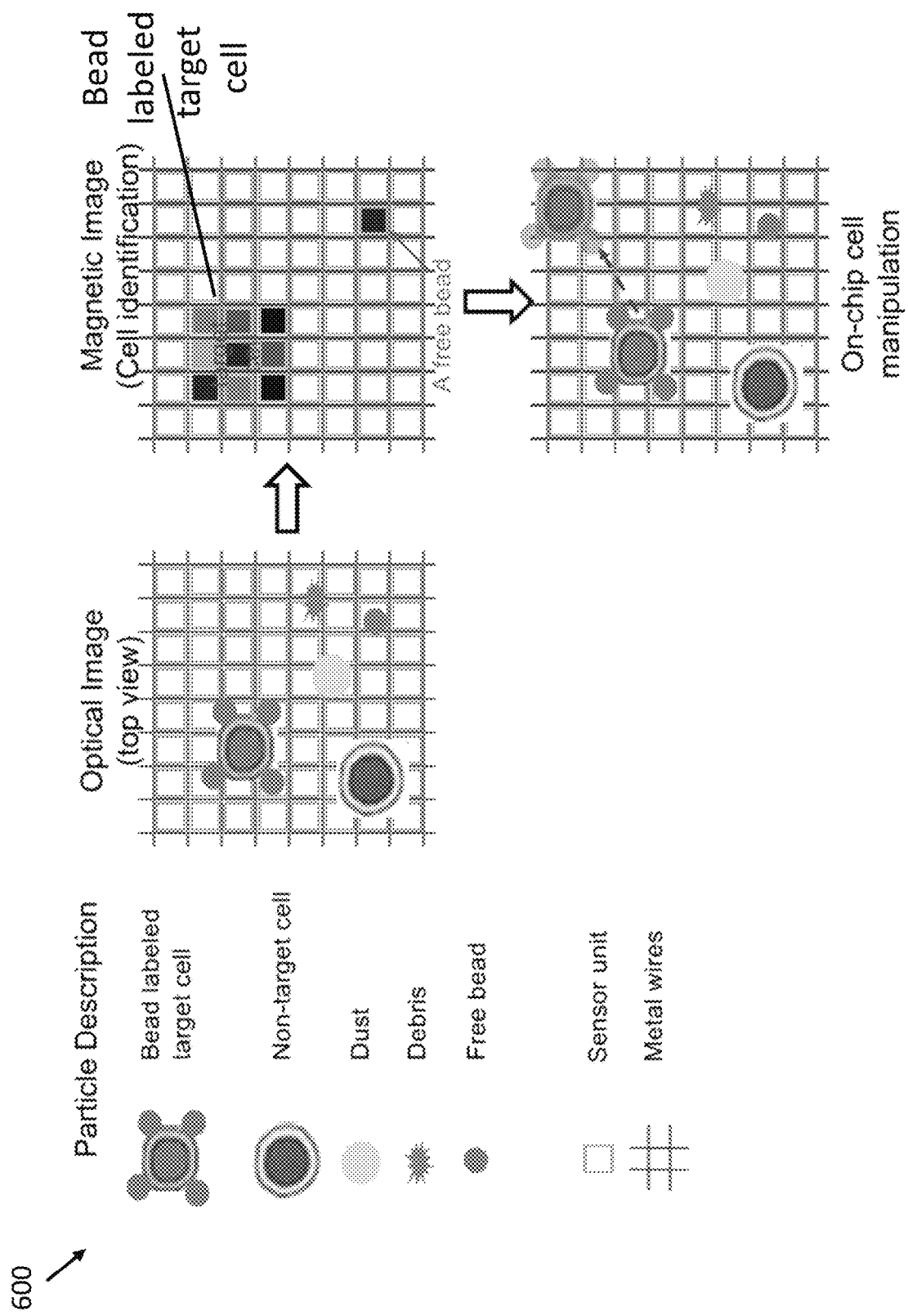
FIG. 6 illustrates a first method of detection of magnetic bead signals from target cells, with various particle types, particle descriptions, particles on the magnetic sensor, and sensor output shown.

FIG. 6 illustrates a first method of detection of magnetic bead signals from target cells, with various particle types, particle descriptions, particles on the magnetic sensor, and sensor output shown. Immunomagnetically isolated cell suspension may be dropped into the sample well (such as illustrated in FIG. 3A), which may hold up to 50 μl of liquid sample. In one implementation, the active chip sensing area is designed to be 1×1 cm comprising 40,000 sensor units (the 8×8 sensor array shown here is merely for illustration purposes). In this regard, the active chip sensing area is several orders of magnitude greater than the size of the bead-labeled target cell. The sample contains bead-labelled target cells and contaminants such as non-target cells, dust, debris and free beads. These particles fall to the surface of the sensing area by gravity and their magnetic signals are detected by the underlying sensor units. Contaminants such as dust, debris and non-target cells are non-magnetic and therefore are not detected. In this regard, single bead Magnetic detection may be highly sensitive even with minimum sample processing because most biological samples or contaminants (e.g., dusts and debris) have negligible magnetic properties and thus background noise is very low. Target cells (labelled with magnetic beads) cast a large "shadow" area on multiple sensors, whereas possible free beads (4.5 μm in diameter, are much smaller than target cells) are detected only by its nearby sensors. Thus, the system may process samples that are heterogeneous (as opposed to homogeneous) as the system does not need to have purified cells upon introduction.

Most free beads may be pre-filtered by a membrane with 7-μm pores, such as discussed above. As discussed in more detail below, the sensor output may be analyzed in order to identify the bead-labeled target cells. In particular, the bead-labeled target cell may have a certain sensor output signature. The system may analyze the sensor output in order to determine whether the sensor output includes the certain sensor output signature. Further, the system may analyze the sensor output to filter out any sensor output that indicates a free bead is present.

Figure 7A:
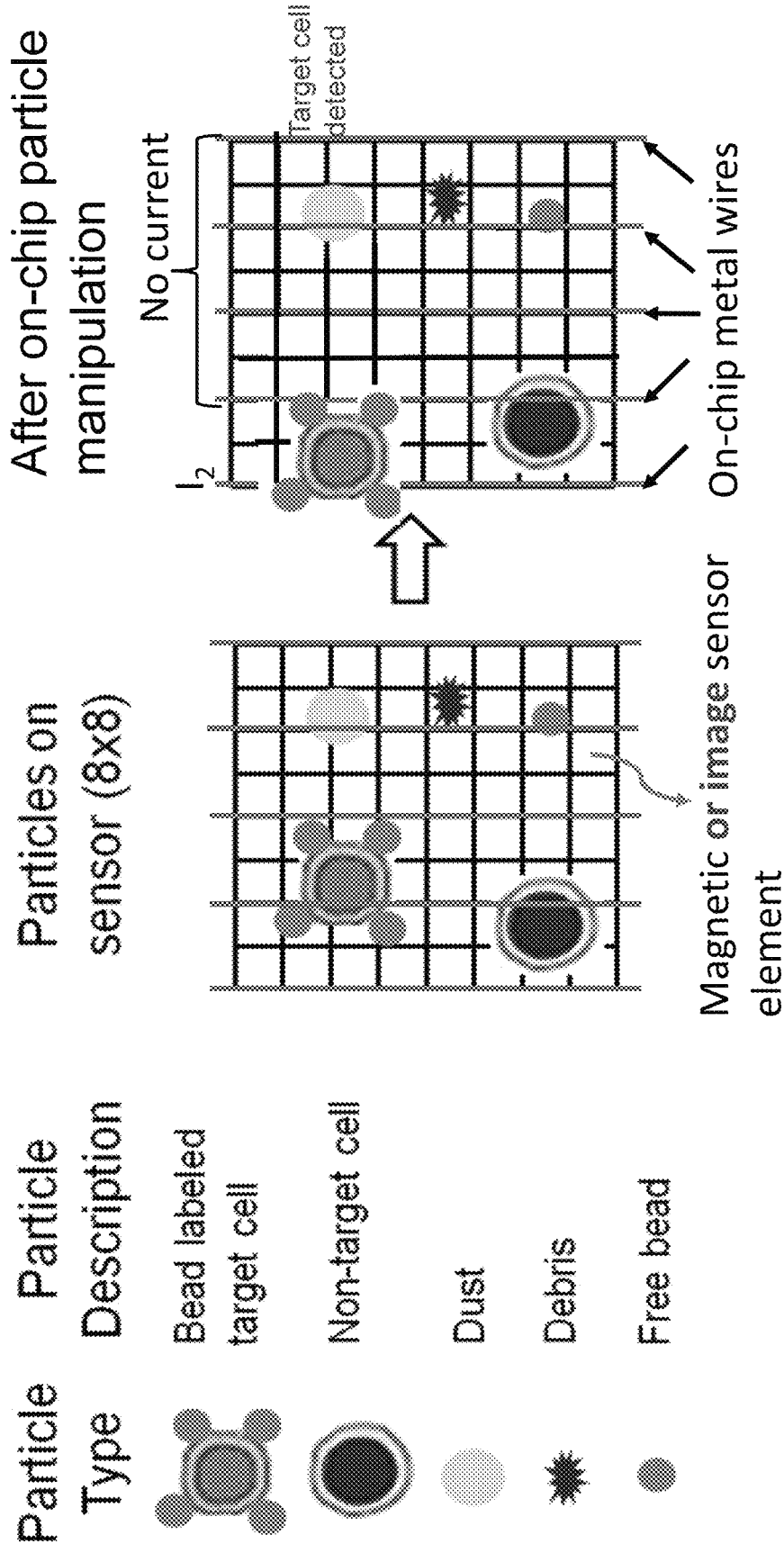
FIG. 7A-B illustrate a second method of detection of target cells based on on-chip magnetic manipulation.
Figure 7B:
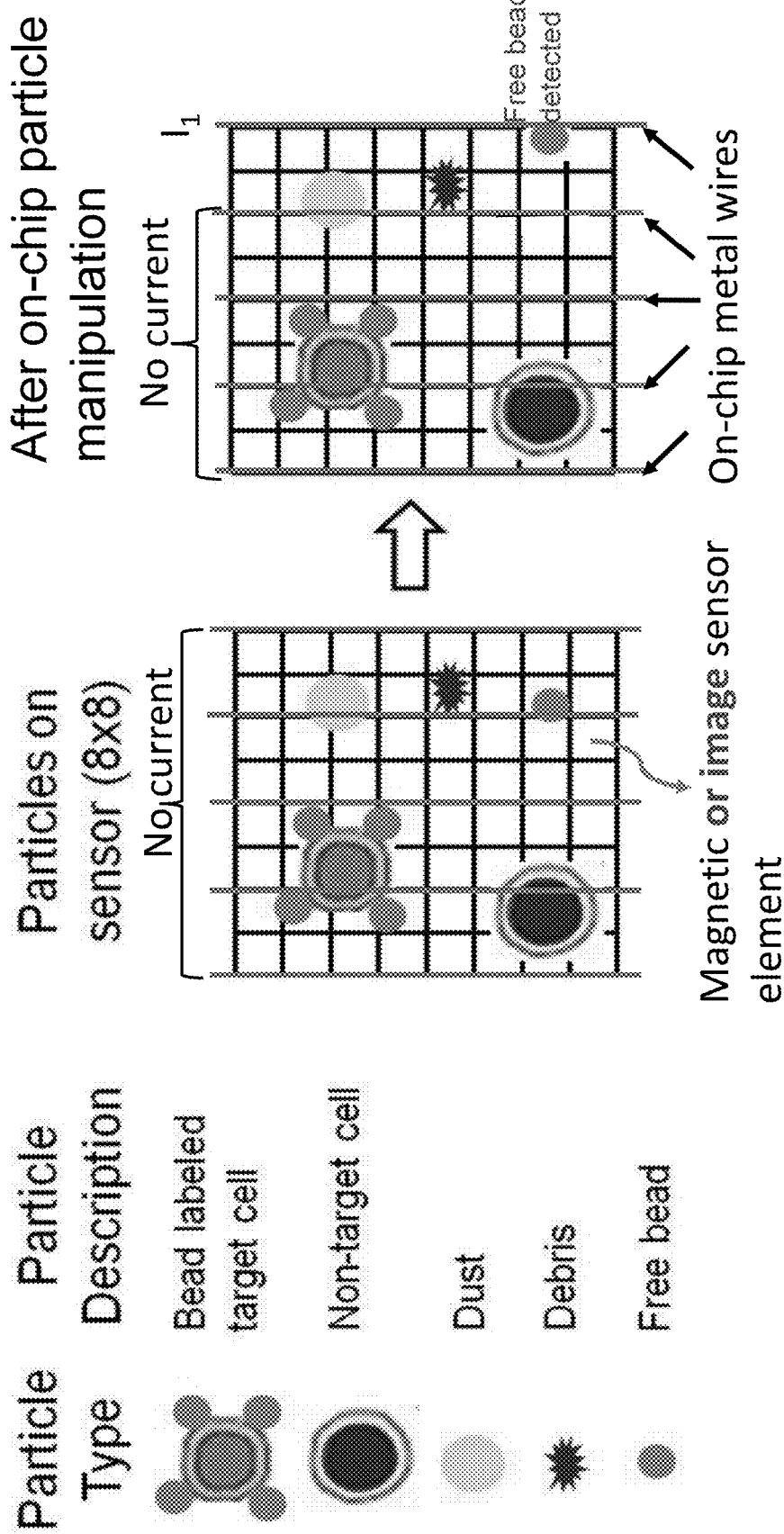

FIG. 7A-B illustrate a second method of detection of target cells based on on-chip magnetic manipulation. More specifically, FIG. 7A illustrates bead-labeled target cell detection (as shown by movement of the bead-labeled target cell). FIG. 7B illustrates free bead detection (as shown by movement of the free bead). In particular, magnetic manipulation may result in movement of the bead-labeled target cell and/or free beads. As discussed above, the movement of the bead-labeled target cell may be determined using a magnetic sensor element (such as a Hall effect sensor) or using an image sensor element.

The system may generate a magnetic field tailored to move certain particles in the well. For example, the system may control the current (thereby modifying the applied magnetic field in order to manipulate which items (e.g., free beads or bead-labeled target cells) are detected), as discussed above. In particular, the system may use varying currents (e.g., first a lower current to detect the movement of the free beads and then a higher current to detect the bead labeled target cells). Thus, the system may vary the AC current magnitude and/or vary the AC current frequency in detecting the bead-labeled target cells.

FIG. 7A illustrates bead-labeled target cell detection by determining movement of the bead-labeled target cell. In particular, on the left side of FIG. 7A, the particles are on the sensor without being subject to magnetic manipulation. On the right side of FIG. 7A, a section of the sensor area is subject to on-chip magnetic manipulation. This is illustrated by the current $I_2$ flowing through only a part of the sensor area. As a result of the current flow (and the magnetic field generated thereby), the bead-labeled target cell moves. This movement may be detected by the Hall effect sensor or an image sensor, which may compare the respective sensor readings both before and after the magnetic field is applied. FIG. 7B illustrates free bead detection (as shown by movement of the free bead). Similar to FIG. 7A, FIG. 7B uses a current $I_1$ to move a free bead. Further, non-target cells (such as white blood cells which do not have a magnetic bead bound thereto), will not move (or will move less than the CTCs bound to the beads).

Figure 8:
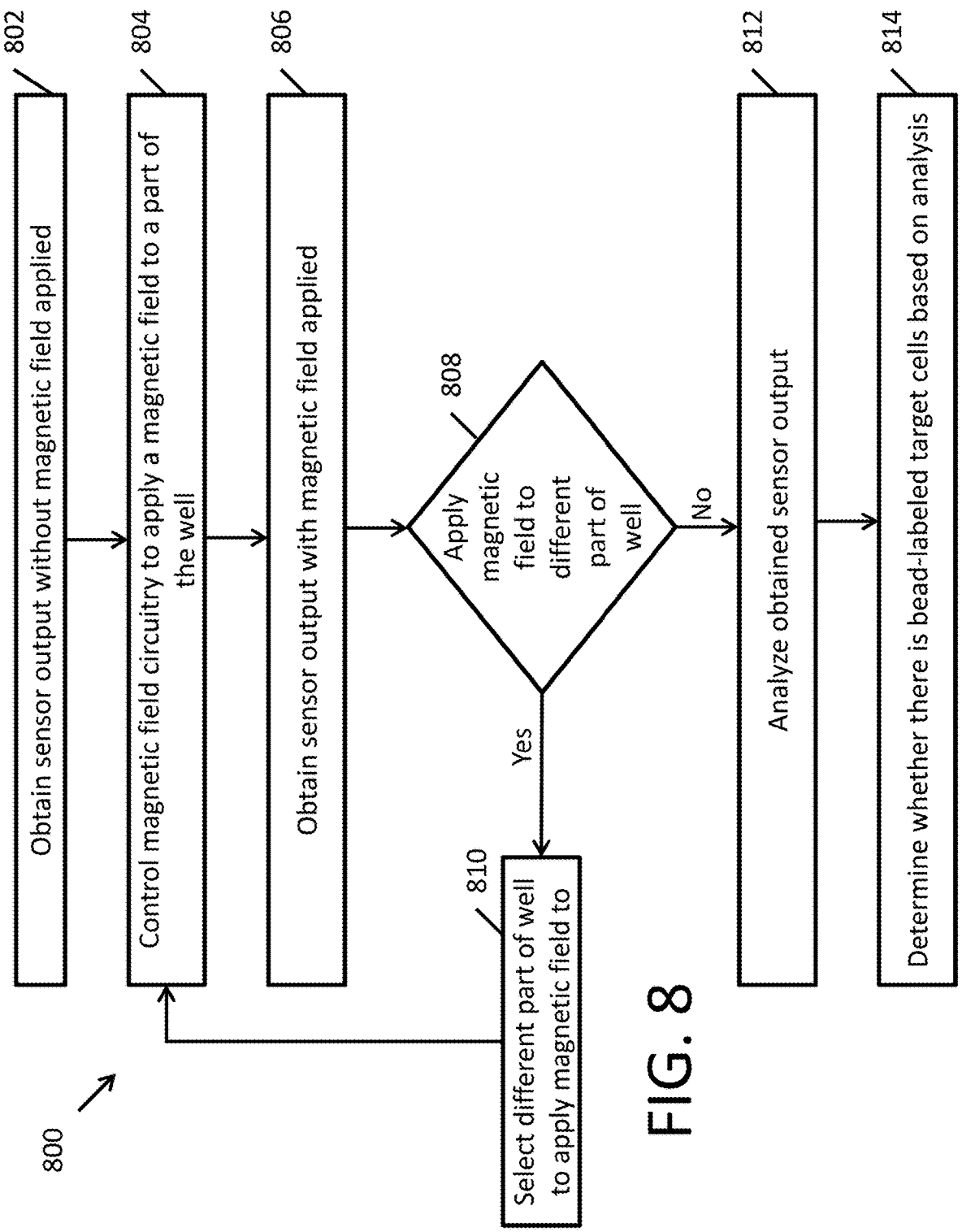
FIG. 8 is a flow chart of an example method of detecting bead-labeled target cells via on-chip magnetic manipulation.

FIG. 8 is a flow chart 800 of an example method of detecting bead-labeled target cells via on-chip magnetic manipulation. At 802, the sensor output is obtained without a magnetic field being applied. At 804, the magnetic field circuitry are controlled (such as sending current through one or more wires) in order to apply a magnetic field to a part of the well. This is illustrated, for example, in FIGS. 7A-B. At 806, the sensor output is obtained with the magnetic field applied. At 808, it is determined whether the magnetic field is applied to a different part of the well. If so, at 810, the different part of the well to apply the magnetic field is selected, and the flow chart 800 loops to 804. If not, at 812, the obtained sensor output is analyzed. At 814, it is determined, based on the analysis, whether there are bead-labeled target cells.

As discussed above, in one implementation, the system may identify target cells that have different bead labels bound to them. For example, a first target cell may have a first bead label bound to it, and a second target cell may have a second bead label bound to it. The bead labels may have different response characteristics. For example, the first bead label may have a quicker response time to an applied magnetic field than the second bead label. As another example, the fluid may have different sized magnetic particles. In particular, the fluid may include a first type of magnetic particle (such as free beads) and a second type of magnetic particle (such as beads bound to CTCs). The first type of magnetic particle may have a different size than the second type of magnetic particle (e.g., the first type of magnetic particle may be smaller than the second type of magnetic particle, as discussed above). In that regard, the system may apply one or more magnetic fields (e.g., one or more AC currents may be used to generate the one or more magnetic fields) in order to identify the different target cells or different types of magnetic particles. Based on the applied magnetic field(s), the system may determine the response. For example, the system may analyze the magnetic sensor output waveform over time to determine the response of the different magnetic bead labels. In the example above of the first bead label having a quicker response time, the system may analyze the response time of the various particles, and determine whether the response time indicates a first bead label or a second bead label. As another example, the system may analyze the magnetic sensor output waveform over time to determine the response of the different types of magnetic particles. In the example above of the free beads having a quicker response time, the system may analyze the response time of the various particles, and determine whether the response time indicates movement of free beads or movement of beads bound to CTCs.

Figure 9A:
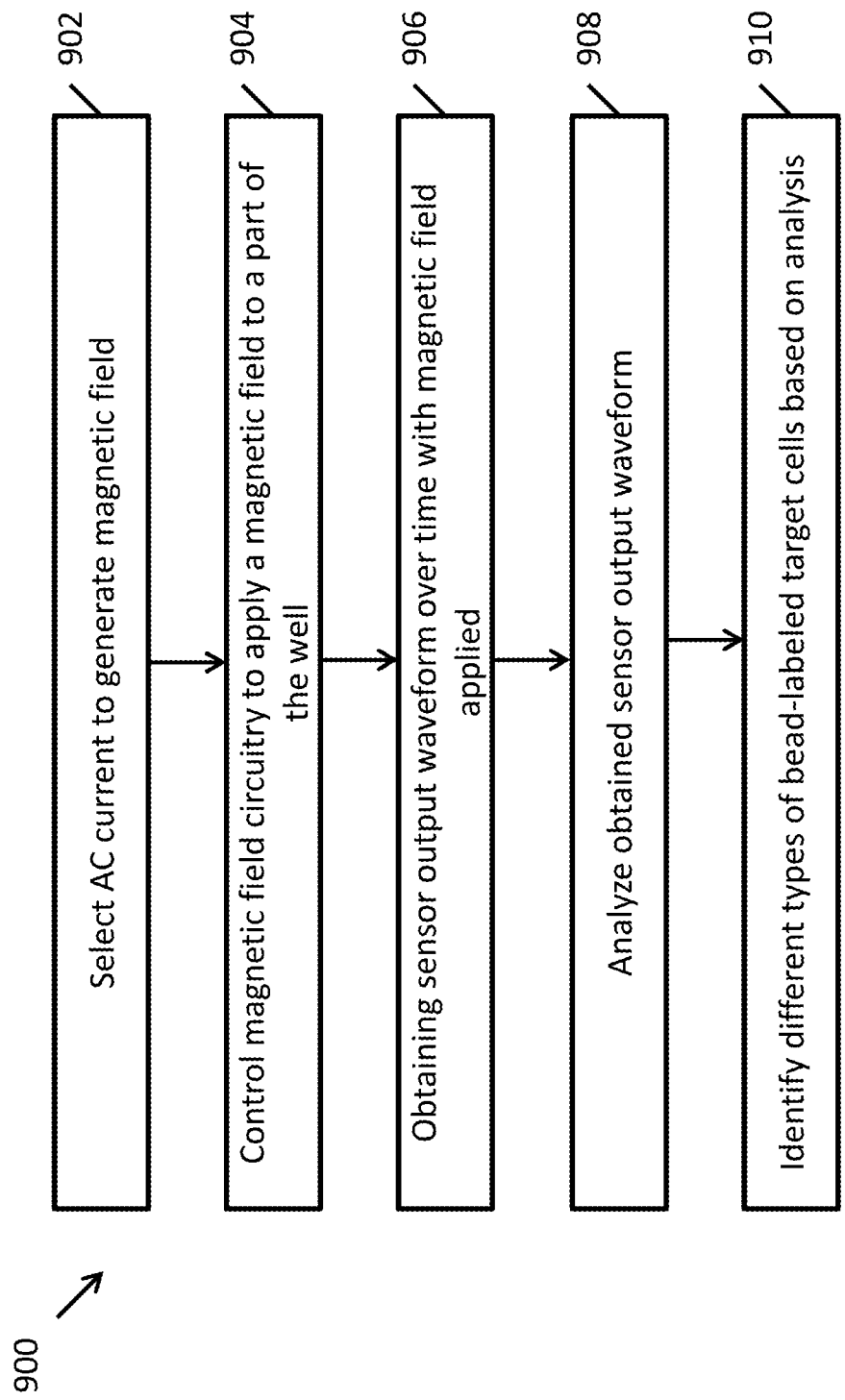
FIG. 9A is a flow chart of an example method of detecting multiple bead-labeled target cells.

FIG. 9A is a flow chart 900 of an example method of detecting multiple bead-labeled target cells using a magnetic field sensor (such as a Hall effect sensor). At 902, the AC current is selected to generate the magnetic field. At 904, the magnetic field circuitry is controlled, using the selected AC current, to apply a magnetic field to a part of the well. At 906, the sensor output waveform over time with the magnetic field applied is obtained. At 908, the obtained sensor output waveform is analyzed. At 910, the different types of bead-labeled target cells are identified based on the analysis.

Figure 9B:
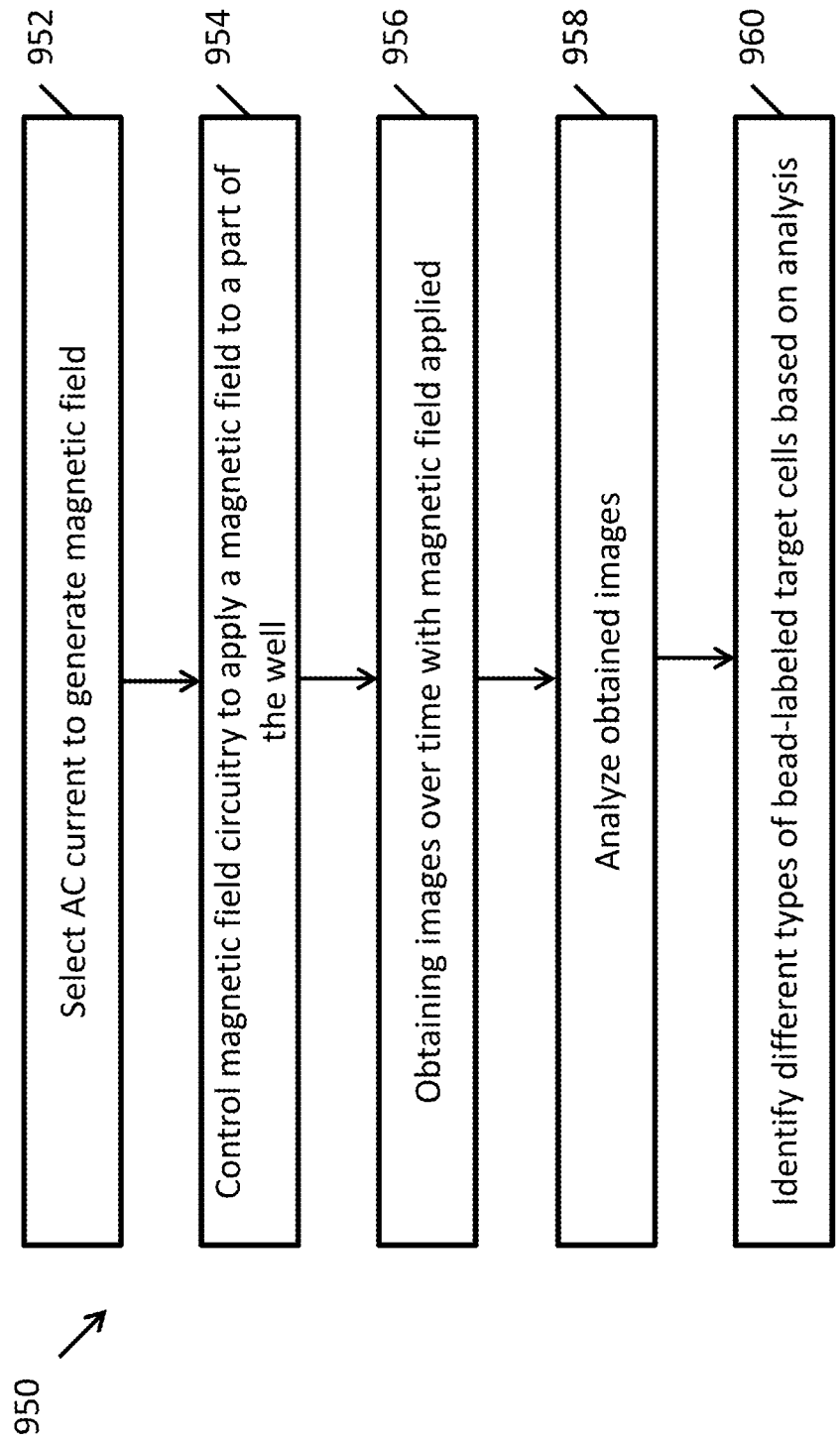
FIG. 9B is a flow chart of another example method of detecting multiple bead-labeled target cells.

FIG. 9B is a flow chart 950 of another example method of detecting multiple bead-labeled target cells using imaging analysis. At 952, the AC current is selected to generate the magnetic field. At 954, the magnetic field circuitry is controlled, using the selected AC current, to apply a magnetic field to a part of the well. At 956, images are obtained over time with the magnetic field applied is obtained. At 958, the obtained images are analyzed. At 960, the different types of bead-labeled target cells are identified based on the analysis.

Figure 10A:
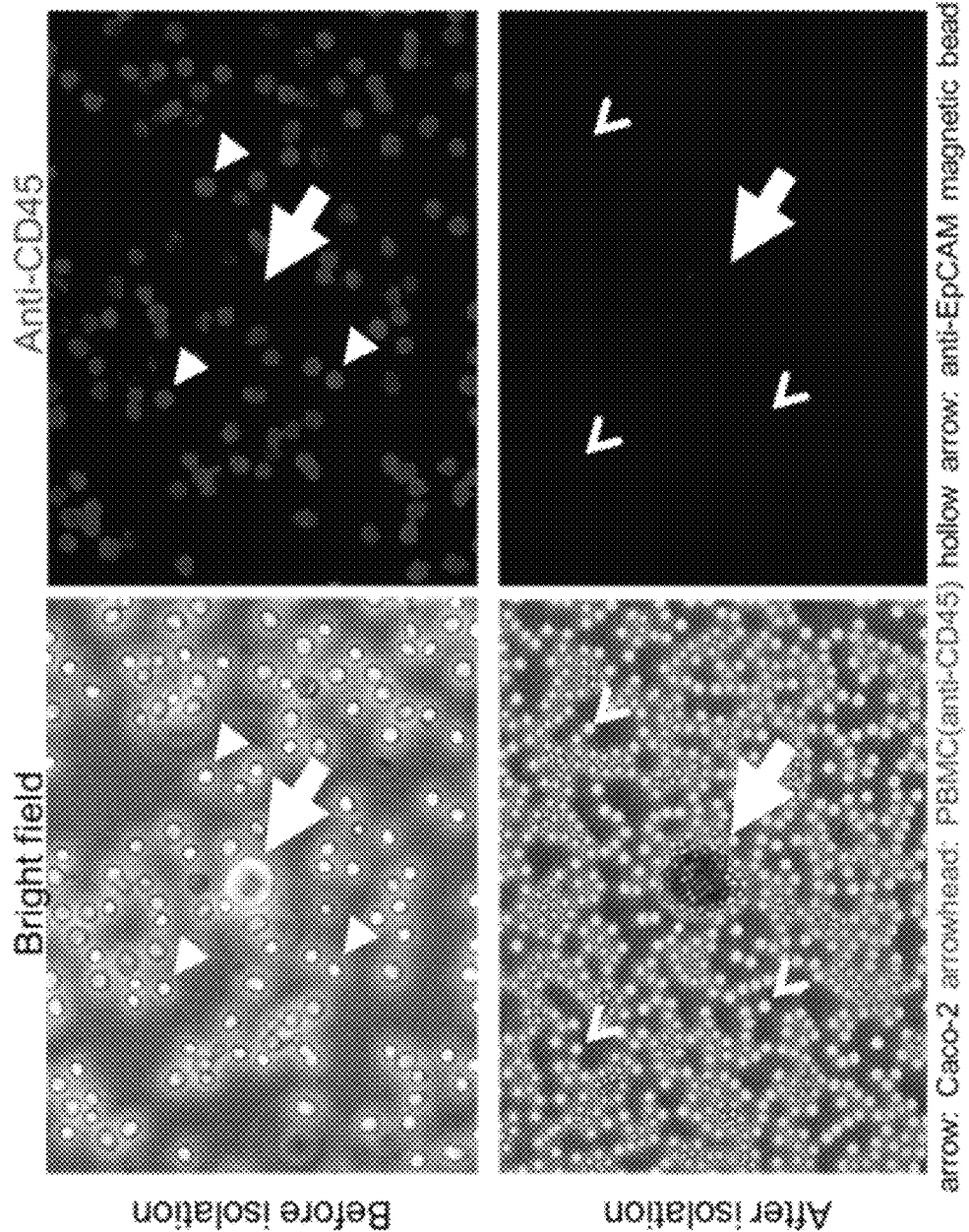
FIG. 10A illustrates magnetic cell isolation using tumor cells in vitro.
Figure 10B:
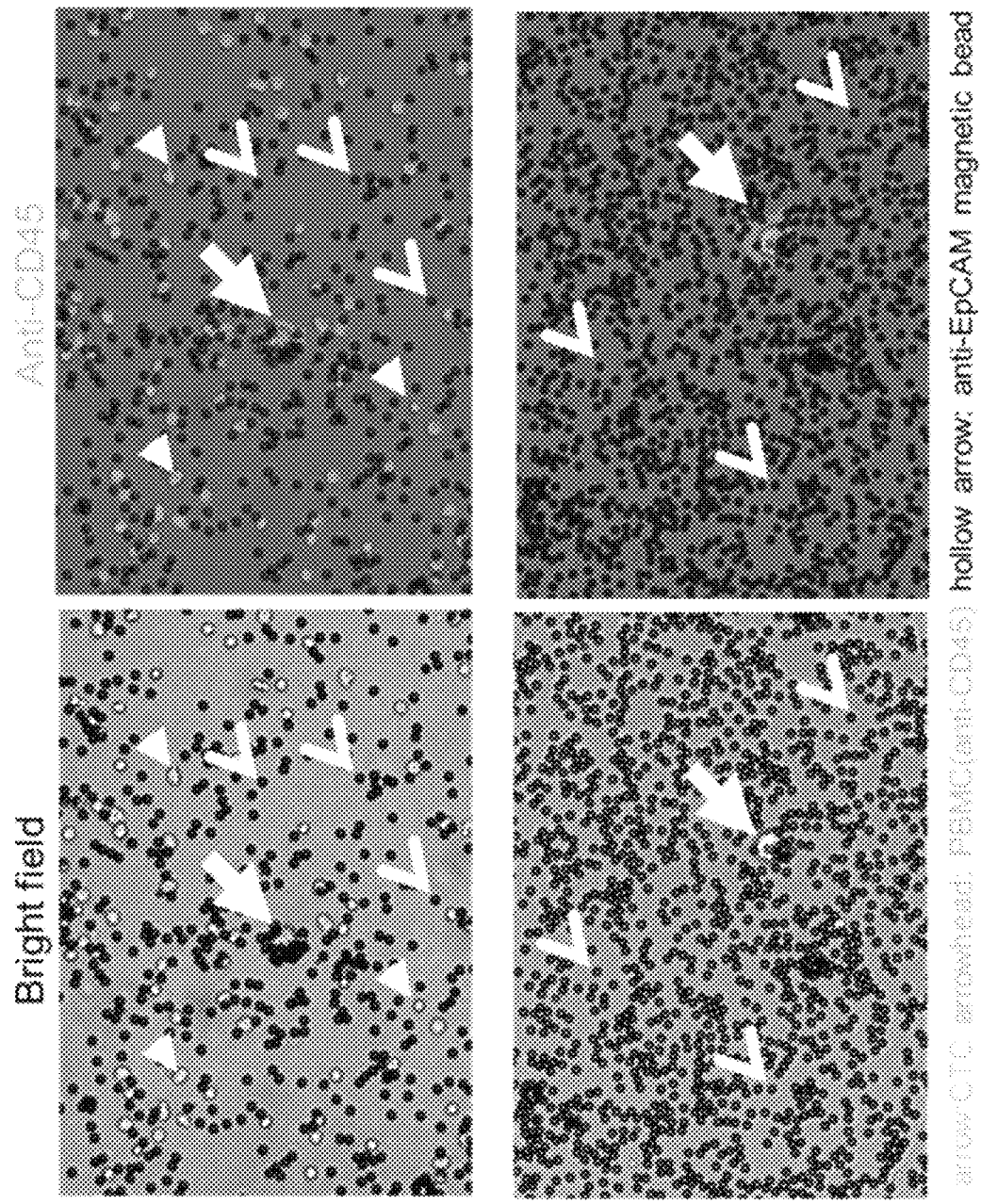
FIG. 10B is a graph of the cancer cell count.
Figure 10C:
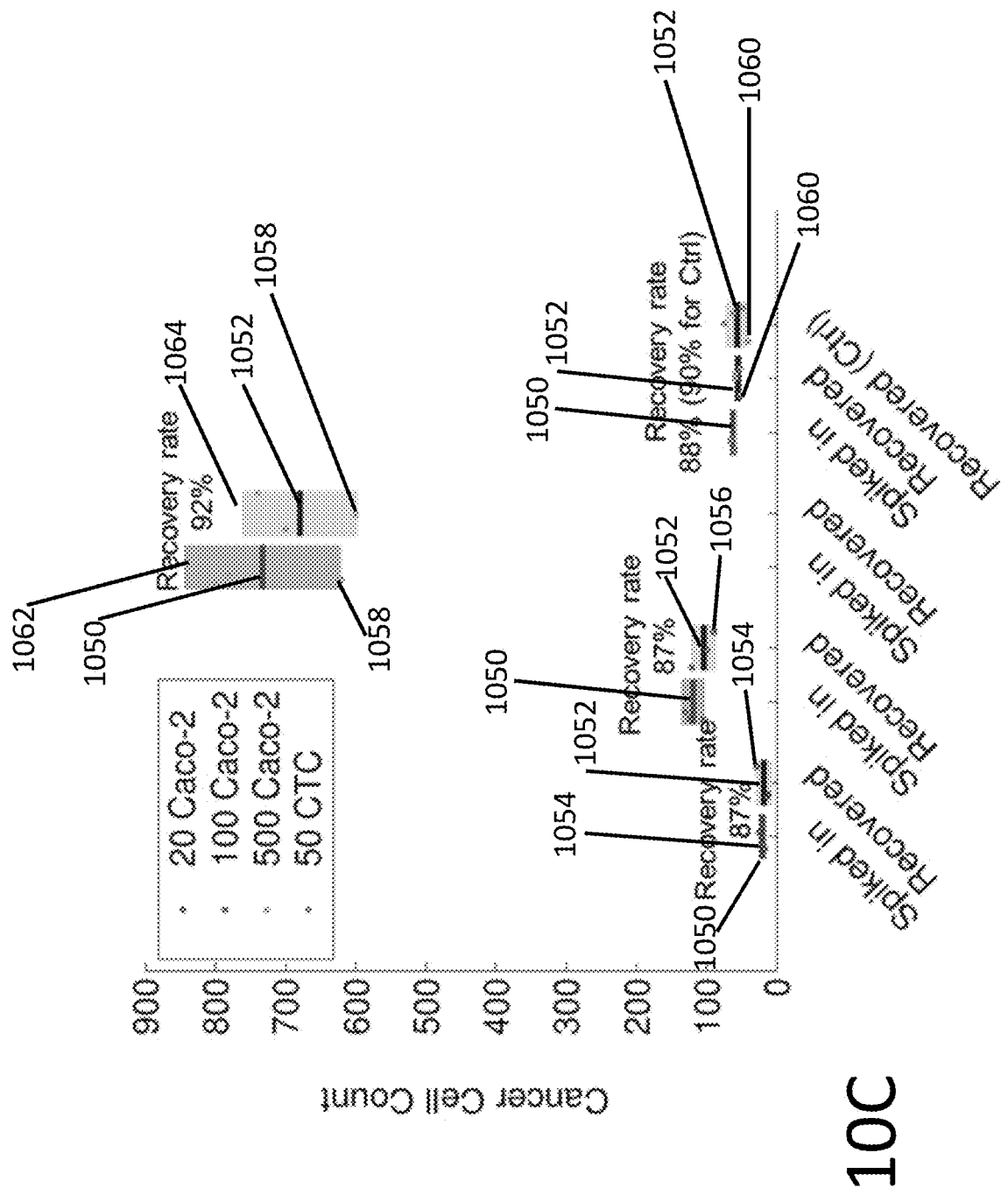
FIG. 10C shows high recovery rate (87-92%) and purity (>99%) with total assay time of only 30 minutes.

For example, a sample may be prepared by spiking different amount of Caco-2 colon cancer cells into $5 \times 10^6$ peripheral blood mononuclear cells (PBMCs). Further, the performance of cell isolation technology may be characterized by three parameters: purity, and recovery, purity and throughput. FIGS. 10A-C illustrate data whereby 20-500 Caco-2 colon cancer cells are inserted into $5 \times 10^6$ peripheral blood mononuclear cells (PBMCs). Thereafter, 4.5-μm-diameter beads conjugated with biotinylated anti-EpCAM antibodies are added for cell isolation. FIG. 10C shows high recovery rate (87-92%) and purity (>99%) with total assay time of only 30 minutes.

In particular, FIGS. 10A-C illustrate evaluation of magnetic cell isolation using tumor cells mixed with PBMCs in vitro. Different amounts of Caco-2 colon cancer cells from serial dilution were spiked into $5 \times 10^6$ human PBMCs (Biolegend, San Diego, Calif.) that mimics the amount of leukocytes in 1 ml peripheral blood. For example, 20 Caco-2 cells are illustrated at 1054, 100 Caco-2 cells are illustrated at 1056, 50 Caco-2 cells are illustrated at 1058, and 50 CTC are illustrated at 1060. Caco-2 cells were stained with Alexa Fluor® 594 anti-human CD45 antibodies (Biolegend). Cell suspensions were mixed with CELLection® biotin binder magnetic beads (Invitrogen, Carlsbad, Calif.) coated with anti-EpCAM antibodies (Biolegend) and isolated with a magnet (Invitrogen), following antibody conjugation and magnetic cell isolation protocols. Numbers of spiked Caco-2 cells were estimated by counting at the transmitted light channel whereas recovered Caco-2 cells and contaminating PBMCs were identified by morphology (transmitted light) and anti-CD45 staining (red fluorescence) (FIG. 10A). In experiments, EGFP-expression breast cancer patient derived CTC cells (about 50) stained with CellTracker Red (Thermo Fisher) from serial dilution were spiked into $5 \times 10^6$ human PBMCs (Biolegend) labeled with Alexa Flour 488 anti-human CD45 antibodies (Biolegend). CTCs and PBMCs were identified by morphology (transmitted light) and fluorescence imaging (green: anti-CD45; yellow: CTC) (FIG. 10B). After cell isolation, no PBMCs are visible in both cases. Recovery rate is defined by the ratio of the mean of recovered cell counts to the mean of spiked cell counts. Cell counts (FIG. 10C) are displayed from triplicate measurements with the mean (1050 and 1052 lines), 95% confidence interval (or 1.96-SEM, 1062 and 1064 (or the boxes around lines 1050 and 1052)). Recovery rate was 87%-92% for Caco-2s and CTCs. Control experiments were also run by recovering Caco2 and CTC cells from buffers (no PBMC mixing). No significant difference is observed. Total assay time of 30 minutes was achieved based on the indirect technique protocol with further optimization of antibody concentration, wash and centrifuge time.

Magnetic particles used in magnetic cell isolation are available in a range of sizes and can be divided into two categories: magnetic nanopacticles (MNPs) or microbeads. Compared to MNPs, microbeads are less susceptible to endocytosis, and not likely to interfere with a cell's structure. The magnetic particles used in the data illustrated in FIGS. 10A-C are 4.5-μm microbeads. These beads comprise many MNPs that are dispersed in a polymer matrix (FIG. 2B). The MNPs are randomly oriented when no magnetizing field (H) is applied so the net bead field is zero; when a magnetizing field is applied, the MNPs will align with H and there will be an induced bead field. This superparamagnetic property prevents the beads from clumping and may be used for magnetic detection.

The above-disclosed subject matter is to be considered illustrative, and not restrictive, and the appended claims are intended to cover all such modifications, enhancements, and other embodiments, which fall within the true spirit and scope of the present disclosure. Thus, to the maximum extent allowed by law, the scope of the present embodiments are to be determined by the broadest permissible interpretation of the following claims and their equivalents, and shall not be restricted or limited by the foregoing detailed description. While various embodiments have been described, it will be apparent to those of ordinary skill in the art that many more embodiments and implementations are possible within the scope of the above detailed description. Accordingly, the embodiments are not to be restricted except in light of the attached claims and their equivalents.

The invention claimed is:

1. An apparatus configured to determining whether a magnetic bead labeled to a target cell is present in a fluid, the apparatus comprising
   a well configured to house the fluid containing particles including free beads that are unbound to any cell and the magnetic bead labeled to the target cell;
   a magnetic field generator configured to generate a magnetic field to at least a part of the well;
   one or more sensors configured to generate sensor data; and
   at least one processor in communication with the magnetic field generator and the one or more sensors, the processor configured to:
      control the magnetic field generator in order for the magnetic field generator to generate the magnetic field to the at least a part of the well by:
         sending a first command to the magnetic field generator in order for the magnetic field generator to generate a first magnetic field, the first magnetic field configured to move the free beads within the well but not configured to move the magnetic bead labeled to the target cell; and
         after controlling the magnetic field generator in order for the magnetic field generator to generate the first magnetic field, sending a second command to the magnetic field generator in order for the magnetic field generator to generate a second magnetic field, the second magnetic field configured to move the magnetic bead labeled to the target cell;

receive sensor data from the one or more sensors, the sensor data being sensed after the generated second magnetic field is applied to the at least a part of the well and indicative of whether there is movement of at least one particle in the fluid from a first region of the well to a second region of the well responsive to the generated second magnetic field;

determine, based on the sensor data, whether there is movement of the at least one particle in the fluid from the first region of the well to the second region of the well; and responsive to determining that there is movement of the at least one particle in the fluid from the first region of the well to the second region of the well, determine that the magnetic bead labeled to the target cell is present in the fluid.

2. The apparatus of claim 1, wherein the one or more sensors comprises one or more optical sensors configured to generate optical sensor data indicative of the movement from the first region of the well to the second region of the well; and wherein the optical sensor data is used to determine whether there is movement of the at least one particle from the first region of the well to the second region of the well.

3. The apparatus of claim 2, wherein the processor is configured to control the one or more optical sensors, based on the control of the magnetic field generator, in order for the one or more optical sensors to generate the optical sensor data indicative of the movement of the magnetic bead labeled to the target cell.

4. The apparatus of claim 3, wherein the processor is configured to time, based on timing of control of the magnetic field generator, sending of commands to the one or more optical sensors, the commands indicative to the one or more optical sensors to generate the sensor data.

5. The apparatus of claim 1, wherein the one or more sensors comprises one or more magnetic sensors configured to generate magnetic sensor data, the one or more magnetic sensors arranged in a grid defining at least the first region and the second region in the well, the magnetic sensor data indicative of the movement in the well from the first region of the well to the second region of the well; and wherein the magnetic sensor data is used to determine whether there is movement of the at least one particle from the first region of the well to the second region of the well.

6. The apparatus of claim 1, wherein a size of the target cell is no greater than 50 microns;

wherein the one or more sensors comprise one or more magnetic sensors comprising a surface area, the one or more magnetic sensors being configured to generate an output indicative of sensing a magnetic characteristic of the magnetic bead labeled to the target cell; and wherein the surface area of the one or more magnetic sensors is at least an order of magnitude greater than the size of the target cell.

7. The apparatus of claim 6, wherein the processor is configured to analyze the sensor data by analyzing sensor output waveforms from the one or more magnetic sensors in order to distinguish between different sized magnetic particles.

8. A method for determining that a magnetic bead labeled to a target cell is present in a fluid, the method comprising:

introducing the fluid containing particles, including free beads that are unbound to any cell and the magnetic bead labeled to the target cell, into a well;

controlling generation of a magnetic field such that the magnetic field is applied to different parts of the well at different times by:

sending a first command to a magnetic field generator in order for the magnetic field generator to generate a first magnetic field, the first magnetic field moving the free beads within the well but not moving the magnetic bead labeled to the target cell; and sending a second command to the magnetic field generator in order for the magnetic field generator to generate a second magnetic field, the second magnetic field moving the magnetic bead labeled to the target cell;

receiving sensor data from one or more sensors, the sensor data being sensed after the generated second magnetic field is applied to the at least a part of the well and indicative of whether there is movement of at least one particle in the fluid from a first region of the well to a second region of the well responsive to the generated second magnetic field;

determining, based on the sensor data, whether there is movement of the at least one particle in the fluid from the first region of the well to the second region of the well; and responsive to determining that there is movement of the at least one particle from the first region of the well to the second region of the well, determining that the magnetic bead labeled to the target cell is present.

9. The method of claim 8, wherein the sensor data comprises optical sensor data indicative of movement of the magnetic bead labeled to the target cell through different parts of the well.

10. The method of claim 8, wherein the sensor data comprises magnetic sensor data indicative of movement of the magnetic bead labeled to the target cell through different parts of the well.

11. The method of claim 8, further comprising, after performing a process so that the magnetic bead is labeled to the target cell but before identification of the magnetic bead labeled to the target cell, reducing a number of the free beads in the fluid that are unbound to any cell.

12. The method of claim 11, wherein a size of the free beads that are unbound to any cell is smaller than a size of the magnetic beads that are labeled to the target cell; and wherein reducing the number of magnetic beads comprises filtering the fluid using a filter, wherein the filter is configured to capture particles greater than the size of the free beads in the fluid that are unbound to any cell but less than the size of the magnetic beads that are labeled to the target cell.

13. The apparatus of claim 1, wherein responsive to receiving the first command, the magnetic field generator is configured to control at least one of frequency or amplitude of current in order to generate the first magnetic field;

wherein responsive to receiving the second command, the magnetic field generator is configured to control the at least one of the frequency or the amplitude of the current in order to generate the second magnetic field; and wherein the first magnetic field is less than the second magnetic field.

14. The apparatus of claim 1, wherein the magnetic field generator comprises wires positioned relative to the well; and wherein the processor is configured to control the magnetic field generator such that current through the wires are controlled in a sequence in order to move the magnetic bead labeled to the target cell to a predetermined section with regard to the well.

15. The apparatus of claim 14, wherein the predetermined section comprises a reservoir.

16. The apparatus of claim 1, wherein the magnetic field generator comprises wires positioned relative to the well; and wherein, based on feedback from the received sensor data, the processor is configured to control current through the wires of the magnetic field generator.

17. The method of claim 8, wherein responsive to receiving the first command, the magnetic field generator controls at least one of frequency or amplitude of current in order to generate the first magnetic field;

wherein responsive to receiving the second command, the magnetic field generator controls the at least one of the frequency or the amplitude of the current in order to generate the second magnetic field; and wherein the first magnetic field is less than the second magnetic field.

18. The method of claim 8, wherein a magnetic field generator comprises wires positioned relative to the well; and wherein controlling generation of the magnetic field comprises controlling current through the wires in a sequence in order to move the magnetic bead labeled to the target cell to a predetermined section with regard to the well.

* * * * *